(12) United States Patent
Thissen

(10) Patent No.: US 11,696,677 B2
(45) Date of Patent: Jul. 11, 2023

(54) STEERABLE INSTRUMENT COMPRISING A CILINDRICAL DIAMETER ADAPTATION SECTION

(71) Applicant: Fortimedix Assets II B.V., Geleen (NL)

(72) Inventor: Mattheus Hendrik Louis Thissen, Swalmen (NL)

(73) Assignee: FORTIMEDIX ASSETS II B.V., Nuth (NL)

( * ) Notice: Subject to any disclaimer, the term of this patent is extended or adjusted under 35 U.S.C. 154(b) by 262 days.

(21) Appl. No.: 16/305,900

(22) PCT Filed: May 31, 2017

(86) PCT No.: PCT/NL2017/050350
§ 371 (c)(1),
(2) Date: Nov. 30, 2018

(87) PCT Pub. No.: WO2017/213491
PCT Pub. Date: Dec. 14, 2017

(65) Prior Publication Data
US 2020/0121166 A1    Apr. 23, 2020

(30) Foreign Application Priority Data
Jun. 6, 2016 (NL) ..................... 2016900

(51) Int. Cl.
*A61B 1/005* (2006.01)
*A61B 1/008* (2006.01)
(Continued)

(52) U.S. Cl.
CPC ............ *A61B 1/0055* (2013.01); *A61B 1/008* (2013.01); *A61B 1/0057* (2013.01); *A61B 1/0052* (2013.01);
(Continued)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS 8,740,884 B2 * 6/2014 Verbeek ............. A61B 1/00135
606/1
8,986,317 B2 * 3/2015 Verbeek ............... A61B 1/0055
219/121.72
(Continued)

FOREIGN PATENT DOCUMENTS

DE    10 2009 037 030 A1    2/2011
DE    10 2010 000 787 A1    7/2011
(Continued)

*Primary Examiner* — Ryan N Henderson
(74) *Attorney, Agent, or Firm* — N.V. Nederlandsch Octrooibureau

(57) ABSTRACT

A steerable instrument for endoscopic and/or invasive type of applications, such as in surgery, which has an elongated tubular body having a proximal end part with a first actuation flexible zone having a first diameter and a distal end part having a first distal flexible zone having a second diameter that is different from the first diameter. A cylindrical diameter adaptation section is arranged to connect the proximal end part to the distal end part such that a flexion in a radial direction relative to a longitudinal center axis of the longitudinal tubular body of the first actuation flexible zone results in an amplified or attenuated flexion of the first distal flexible zone.

12 Claims, 16 Drawing Sheets

(51) Int. Cl.
*A61B 1/00* (2006.01)
*A61B 17/29* (2006.01)
*A61B 17/00* (2006.01)
*A61M 25/01* (2006.01)

(52) U.S. Cl.
CPC ........... *A61B 1/00071* (2013.01); *A61B 17/29* (2013.01); *A61B 2017/00309* (2013.01); *A61B 2017/00323* (2013.01); *A61B 2017/2905* (2013.01); *A61M 25/0138* (2013.01)

(58) Field of Classification Search
CPC ... A61B 1/0056; A61B 1/0057; A61B 1/0058; A61B 1/008; A61B 2017/003; A61B 2017/00305; A61B 2017/00309; A61B 2017/00314; A61B 2017/00318; A61B 2017/00323; A61B 2017/00327; A61M 25/0133; A61M 25/0138
See application file for complete search history.

(56) References Cited

U.S. PATENT DOCUMENTS

| | | | | |
|---|---|---|---|---|
| 9,039,676 | B2* | 5/2015 | Klima | A61M 25/0138 |
| | | | | 604/95.04 |
| 9,468,359 | B2* | 10/2016 | Weisshaupt | A61B 1/00149 |
| D796,672 | S * | 9/2017 | Nijsten | D24/138 |
| 9,848,858 | B2* | 12/2017 | Verbeek | B25J 18/06 |
| 10,328,241 | B2* | 6/2019 | Verbeek | A61B 1/0055 |
| 2003/0149338 | A1 | 8/2003 | Francois et al. | |
| 2004/0199051 | A1* | 10/2004 | Weisel | A61B 17/29 |
| | | | | 600/141 |
| 2005/0096694 | A1* | 5/2005 | Lee | A61B 17/062 |
| | | | | 606/205 |
| 2005/0273085 | A1* | 12/2005 | Hinman | A61M 25/0138 |
| | | | | 606/1 |
| 2007/0049800 | A1 | 3/2007 | Boulais | |
| 2008/0234545 | A1* | 9/2008 | Breedveld | A61M 25/0054 |
| | | | | 600/104 |
| 2009/0069632 | A1* | 3/2009 | McIntyre | A61B 1/0055 |
| | | | | 600/146 |
| 2009/0299343 | A1* | 12/2009 | Rogers | A61M 25/0053 |
| | | | | 606/1 |
| 2010/0287755 | A1 | 11/2010 | Korner | |
| 2010/0318067 | A1* | 12/2010 | Klima | A61M 25/0138 |
| | | | | 604/528 |
| 2011/0004157 | A1* | 1/2011 | Dewaele | A61B 1/01 |
| | | | | 604/95.01 |
| 2011/0034764 | A1* | 2/2011 | Verbeek | A61M 25/0013 |
| | | | | 600/101 |
| 2011/0065990 | A1* | 3/2011 | Verbeek | A61M 25/0138 |
| | | | | 600/142 |
| 2012/0116163 | A1* | 5/2012 | Lutze | A61B 1/00071 |
| | | | | 600/118 |
| 2012/0130173 | A1* | 5/2012 | Lutze | A61B 17/00 |
| | | | | 600/146 |
| 2012/0277730 | A1* | 11/2012 | Salahieh | A61B 1/00135 |
| | | | | 604/528 |
| 2012/0323077 | A1* | 12/2012 | Verbeek | A61B 1/0055 |
| | | | | 600/146 |
| 2014/0207151 | A1* | 7/2014 | Verbeek | A61B 17/00234 |
| | | | | 606/130 |
| 2014/0276966 | A1* | 9/2014 | Ranucci | A61B 17/07207 |
| | | | | 606/139 |
| 2015/0107396 | A1 | 4/2015 | Suehara | |
| 2015/0112134 | A1 | 4/2015 | Suehara et al. | |
| 2015/0157353 | A1 | 6/2015 | Lenker et al. | |
| 2016/0015249 | A1 | 1/2016 | Suehara | |
| 2016/0096004 | A1 | 4/2016 | Gerrans et al. | |
| 2017/0027607 | A1* | 2/2017 | Verbeek | A61B 17/0218 |
| 2018/0008805 | A1* | 1/2018 | Pleijers | A61B 17/29 |
| 2018/0099119 | A1* | 4/2018 | Verbeek | A61B 1/0055 |
| 2018/0242962 | A1* | 8/2018 | Walen | A61B 1/0051 |
| 2019/0231169 | A1* | 8/2019 | Thissen | A61B 1/00073 |
| 2019/0255291 | A1* | 8/2019 | Verbeek | A61B 17/00234 |
| 2020/0030576 | A1* | 1/2020 | Verbeek | A61M 25/0138 |
| 2020/0121166 | A1* | 4/2020 | Thissen | A61B 1/0055 |
| 2020/0129166 | A1* | 4/2020 | Thissen | A61B 17/29 |

FOREIGN PATENT DOCUMENTS

| | | | |
|---|---|---|---|
| DE | 10 2010 005 243 | A1 | 7/2011 |
| EP | 2 762 058 | A1 | 8/2014 |
| WO | 97/42910 | A1 | 11/1997 |
| WO | 2006/026520 | A2 | 3/2006 |
| WO | 2006/057702 | A2 | 6/2006 |
| WO | 2006/116457 | A2 | 11/2006 |
| WO | 2007/039875 | A2 | 4/2007 |
| WO | 2008/139768 | A1 | 11/2008 |
| WO | 2009/035812 | A1 | 3/2009 |
| WO | 2009/098244 | A | 8/2009 |
| WO | 2009/112060 | A1 | 9/2009 |
| WO | WO-2009112060 | A1 * | 9/2009 ......... A61B 1/00071 |
| WO | 2009/127236 | A1 | 10/2009 |
| WO | 2010/028090 | A2 | 3/2010 |
| WO | 2010/105649 | A1 | 9/2010 |
| WO | 2010/136272 | A1 | 12/2010 |
| WO | 2010/136274 | A1 | 12/2010 |
| WO | 2010/151698 | A2 | 12/2010 |
| WO | 2011/018179 | A2 | 2/2011 |
| WO | 2011/079897 | A1 | 7/2011 |
| WO | 2012/035531 | A1 | 3/2012 |
| WO | 2012/040430 | A1 | 3/2012 |
| WO | 2012/128618 | A1 | 9/2012 |
| WO | 2012/139869 | A2 | 10/2012 |
| WO | 2012/151396 | A2 | 11/2012 |
| WO | 2012/173478 | A1 | 12/2012 |
| WO | 2014/011049 | A1 | 1/2014 |
| WO | 2015/084174 | A1 | 6/2015 |
| WO | 2015085307 | A1 | 6/2015 |
| WO | 2016/030457 | A1 | 3/2016 |
| WO | 2016/061291 | A1 | 4/2016 |
| WO | 2016/172706 | A1 | 4/2016 |
| WO | 2016/089202 | A1 | 6/2016 |
| WO | 2016/091856 | A1 | 6/2016 |
| WO | 2016/091858 | A1 | 6/2016 |
| WO | 2016/138443 | A2 | 9/2016 |
| WO | 2016/160694 | A1 | 10/2016 |
| WO | 2017/010883 | A2 | 1/2017 |
| WO | 2017/014624 | A1 | 1/2017 |
| WO | 2017/082720 | A1 | 5/2017 |
| WO | 2017/176766 | A1 | 10/2017 |
| WO | 2017/213491 | A1 | 12/2017 |
| WO | 2018/067004 | A1 | 4/2018 |

* cited by examiner

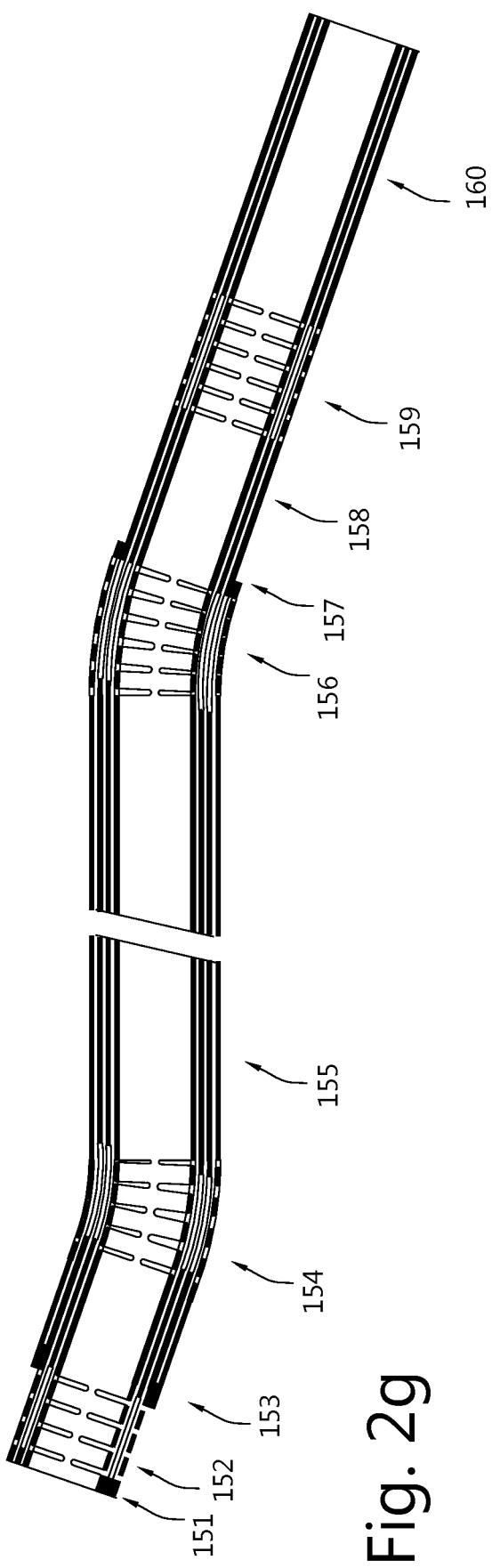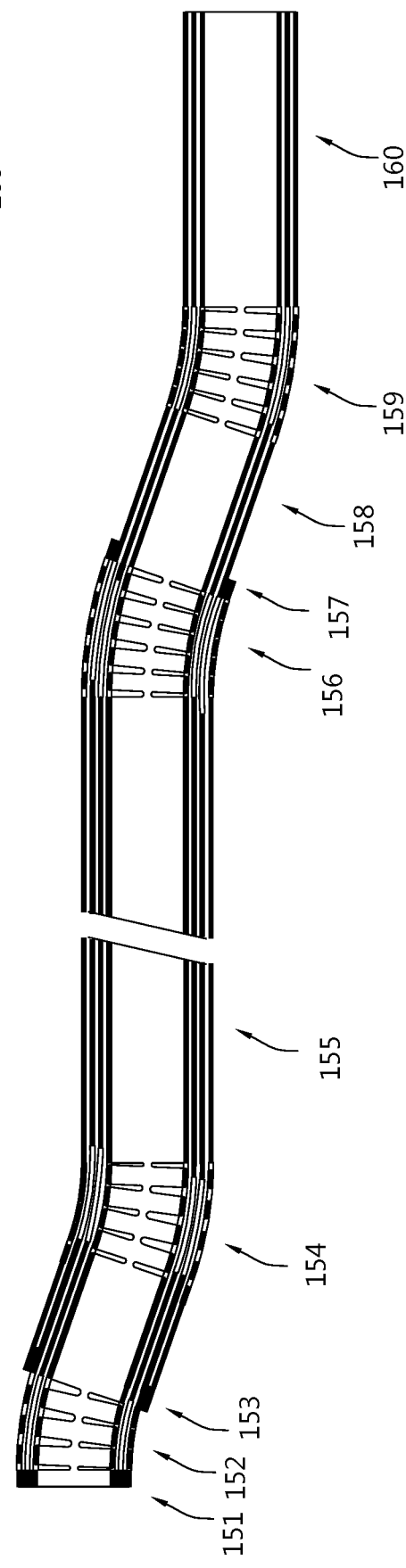

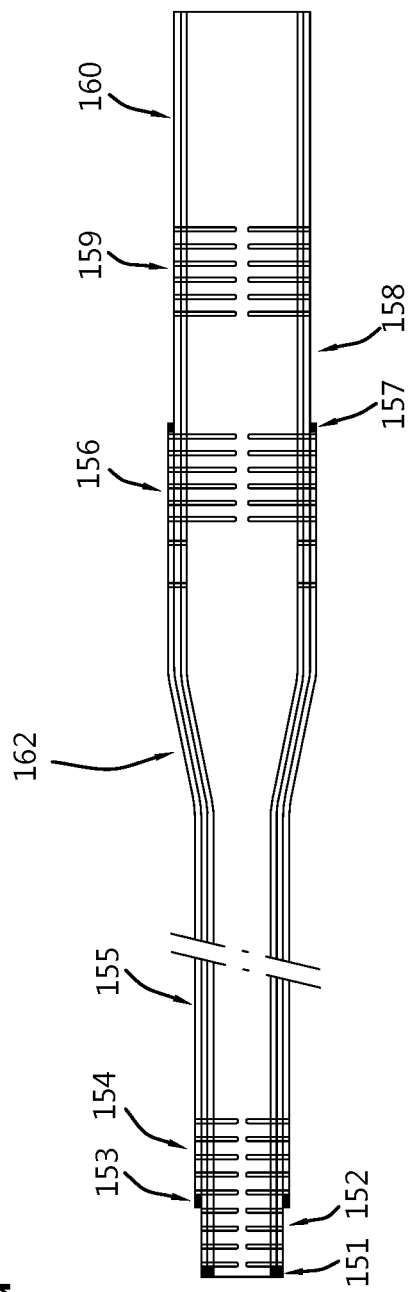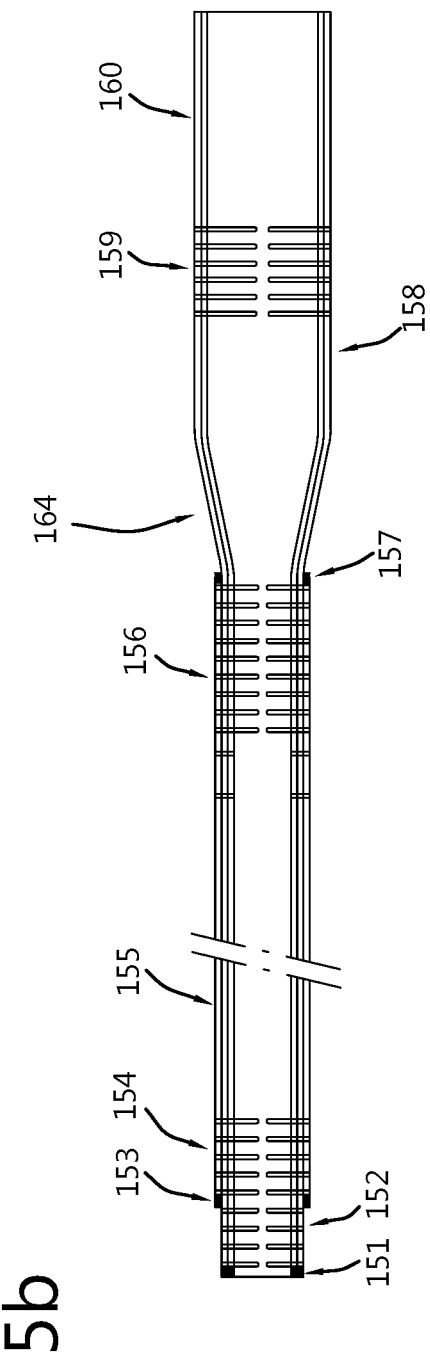

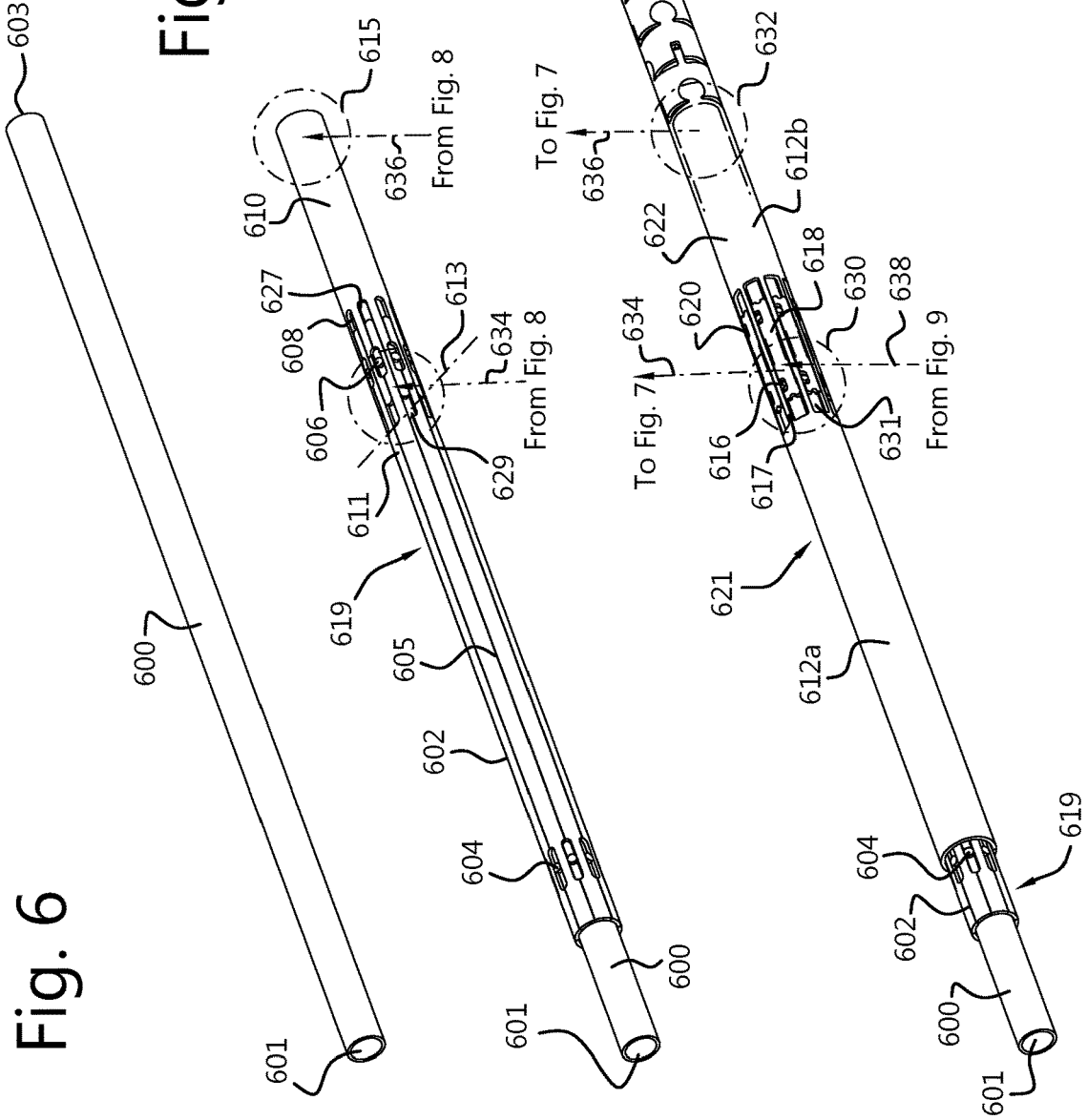

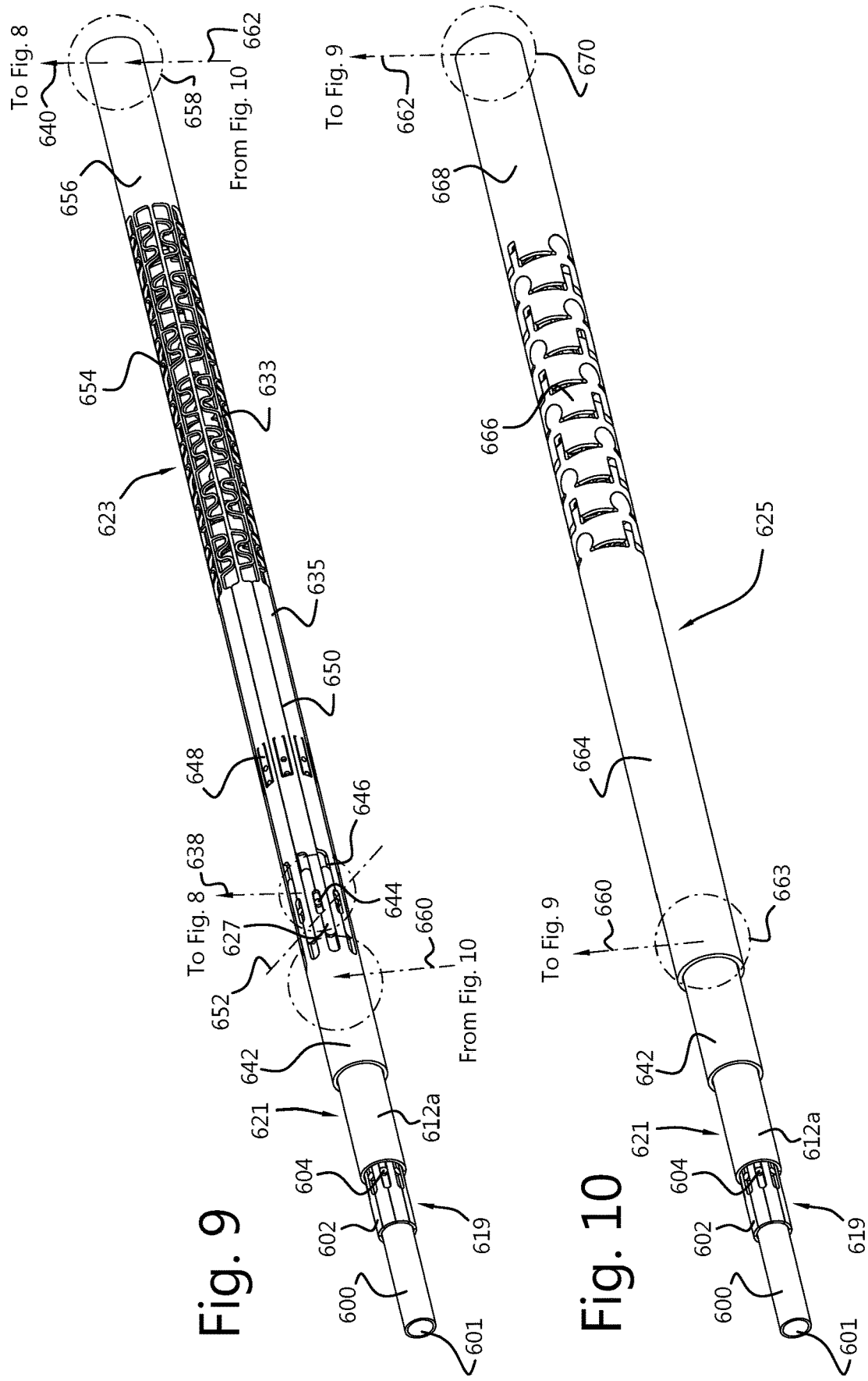

STEERABLE INSTRUMENT COMPRISING A CILINDRICAL DIAMETER ADAPTATION SECTION

The invention relates to a steerable instrument for endoscopic and/or invasive type of applications, such as in surgery, the instrument comprising an elongated tubular body having a cylindrical diameter adaptation section. The steerable instrument according to the invention can be used in both medical and non-medical applications. Examples of the latter include inspection and/or repair of mechanical and/or electronic hardware at locations that are difficult to reach. Hence, terms used in the following description such as endoscopic application or invasive instrument, must be interpreted in a broad manner.

Transformation of surgical interventions that require large incisions for exposing a target area into minimal invasive surgical interventions, i.e. requiring only natural orifices or small incisions for establishing access to the target area, is a well-known and ongoing process. In performing minimal invasive surgical interventions, an operator such as a physician, requires an access device that is arranged for introducing and guiding invasive instruments into the human or animal body via an access port of that body. In order to reduce scar tissue formation and pain to a human or animal patient, the access port is preferably provided by a single small incision in the skin and underlying tissue. In that respect the possibility to use a natural orifice of the body would even be better. Furthermore, the access device preferably enables the operator to control one or more degrees of freedom that the invasive instruments offer. In this way, the operator can perform required actions at the target area in the human or animal body in an ergonomic and accurate manner with a reduced risk of clashing of the instruments used.

Surgical invasive instruments and endoscopes through which these instruments are guided towards the target area are well-known in the art. Both the invasive instruments and endoscopes can comprise a steerable tube that enhances its navigation and steering capabilities. Such a steerable tube preferably comprises a proximal end part including at least one flexible zone, a distal end part including at least one flexible zone, and a rigid intermediate part, wherein the steerable tube further comprises a steering arrangement that is adapted for translating a deflection of at least a part of the proximal end part relative to the rigid intermediate part into a related deflection of at least a part of the distal end part.

Furthermore, the steerable tube preferably comprises a number of co-axially arranged cylindrical elements including an outer element, an inner element and one or more intermediate elements depending on the number of flexible zones in the proximal and distal end parts of the tube and the desired implementation of the steering members of the steering arrangement, i.e. all steering members can be arranged in a single intermediate element or the steering members are divided in different sets and each set of steering members is arranged in a different intermediate member. In most prior art devices, the steering arrangement comprises conventional steering cables with, for instance, sub 1 mm diameters as steering members, wherein the steering cables are arranged between related flexible zones at the proximal and distal end parts of the tube. However, as steering cables have many well-known disadvantages, it is preferred to avoid them and to implement the steering members by one or more sets of longitudinal elements that form integral parts of the one or more intermediate elements. Each of the intermediate elements can be fabricated either by using a suitable material addition technique, such as injection moulding or plating, or by a suitable material removal technique, such as laser cutting, photochemical etching, deep pressing, conventional chipping techniques such as drilling or milling or high-pressure water jet cutting systems. Of the aforementioned material removal techniques, laser cutting is very advantageous as it allows a very accurate and clean removal of material under reasonable economic conditions. Further details regarding the design and fabrication of the abovementioned steerable tube and the steering arrangement thereof have been described for example in WO 2009/112060 A1, WO 2009/127236 A1, U.S. Ser. No. 13/160,949, and U.S. Ser. No. 13/548,935 of the applicant, all of which are hereby incorporated by reference in their entirety.

Steerable invasive instruments typically comprise a handle that is arranged at the proximal end part of the steerable tube for steering the tube and/or for manipulating a tool that is arranged at the distal end part of the steerable tube. Such a tool can for example be a camera, a manual manipulator, e.g. a pair of scissors, forceps, or manipulators using an energy source, e.g. an electrical, ultrasonic or optical energy source.

In this application, the terms "proximal" and "distal" are defined with respect to an operator, e.g. a physician that operates the instrument or endoscope. For example, a proximal end part is to be construed as a part that is located near the physician and a distal end part as a part located at a distance from the physician.

It is known from the prior art that amplification of a flexion of a distal flexible zone of a distal end part of an elongated tubular body of a steerable instrument, i.e. a bending angle of a flexible zone in the distal end part is at least the same and preferably larger than a bending angle of a corresponding flexible zone in the proximal end part of the elongated tubular body, can be achieved by using a proximal end part having a larger diameter than the distal end part. In the event that the proximal end part has a smaller diameter than the distal end part, a flexion in the proximal end part leads to a corresponding attenuated flexion of the distal end part.

Of course, the same technique can be used vice versa such that a proximal deflection to a certain first extent causes a corresponding distal deflection to another second extent which is reduced relative to the first extent.

The requirement for an amplified or attenuated flexion of the distal end part in response to a flexion of the proximal end part depends on the specific intervention for which the steerable instrument is used. Amplified flexion of the distal end part may be required in order to be able to exert a larger force at the operating site and/or to compensate for the loss in response due to stretch of the longitudinal steering elements. Attenuated flexion of the distal end part may be required to improve the maneuverability accuracy of the distal end part. It is known that in order to connect the proximal end part and the distal end part having different diameters a diameter adaptation arrangement is required.

A disadvantage of steerable instruments comprising diameter adaptation arrangements known from the prior art is that the construction of these instruments is quite cumbersome and therefore costly at least in part of the diameter adaptation arrangement. Another disadvantage of steerable instruments comprising known diameter adaptation arrangements is that such arrangements have a reduced reliability as they are more susceptible to failure due to damage. A further disadvantage of steerable instruments comprising known diameter adaptation arrangements is that such arrangements add to the diameter of the elongated tubular bodies of the steerable instruments. In the event that multiple steerable instruments are being used during an intervention, an increased diameter of the elongated tubular bodies of the steerable instruments may compromise their maneuverability which of course is highly undesirable.

Such disadvantages of prior art arrangements have been addressed and solved by the steerable instruments comprising a diameter adaptation arrangement as described in not yet published Dutch patent application NL2015185 filed at Jul. 17, 2015.

It is an object of the invention to provide a steerable instrument for endoscopic and/or invasive type of applications comprising a cylindrical diameter adaptation section, which instrument preempts or at least reduces the disadvantages of steerable instruments comprising known diameter adaptation arrangements mentioned above.

This is achieved by a steerable instrument as claimed in claim 1.

The steerable instrument according to the invention comprises an internally arranged cylindrical diameter adaptation section that adds significantly less to the diameter of the elongated tubular body of the steerable instrument than diameter adaptation arrangements known from the prior art. It also comprises less cylindrical elements than e.g. the one as described in above mentioned, non-published patent application NL2015185. In this way the maneuverability of a steerable instrument according to the invention is improved. In addition, as the cylindrical diameter adaptation section is arranged inside the elongated tubular body of the steerable instrument, the reliability of the steerable instrument according to the invention is improved as it is less vulnerable to damage. Furthermore, the steerable instrument according to the invention can be manufactured in a less cumbersome and therefore less costly way.

In a second aspect, the present invention relates to spacers used between adjacent longitudinal elements in steerable instruments in order to keep adjacent longitudinal elements at a predetermined tangential distance from each other and, therefore, prevent tangential movement of the longitudinal elements as much as possible.

Such spacers are known in the art. Examples of such spacers are e.g. known from WO 2009/112060 A1, WO 2009/127236 A1, U.S. Ser. No. 13/160,949, and U.S. Ser. No. 13/548,935 of the applicant. Another example of such a spacer is described in not yet published PCT patent application PCT/NL2015/050798 filed at Nov. 15, 2015 of the applicant.

It is observed that WO2009112060A discloses spacers between adjacent flexible portions of longitudinal elements in an intermediate cylindrical element, which are shaped as slidable islands. In an embodiment, it is disclosed that these slidable islands are attached, e.g. by laser welding, to another cylindrical element located either inside or outside the intermediate cylindrical element.

Using break islands during the manufacturing of steerable instruments which are broken off by exerting a longitudinal force on them to render separately moveable parts is described in not pre-published application PCT/NL2014/050837.

In its second aspect, the present invention is directed to manufacturing a steerable instrument with spacers between adjacent flexible portions of longitudinal elements.

Such a manufacturing process is claimed in independent claim 14.

Further features and advantages of the invention will become apparent from the description of the invention by way of non-limiting and non-exclusive embodiments. These embodiments are not to be construed as limiting the scope of protection. The person skilled in the art will realize that other alternatives and equivalent embodiments of the invention can be conceived and reduced to practice without departing from the scope of the present invention. Embodiments of the invention will be described with reference to the figures of the accompanying drawings, in which like or same reference symbols denote like, same or corresponding parts, and in which:

Figure 2A:
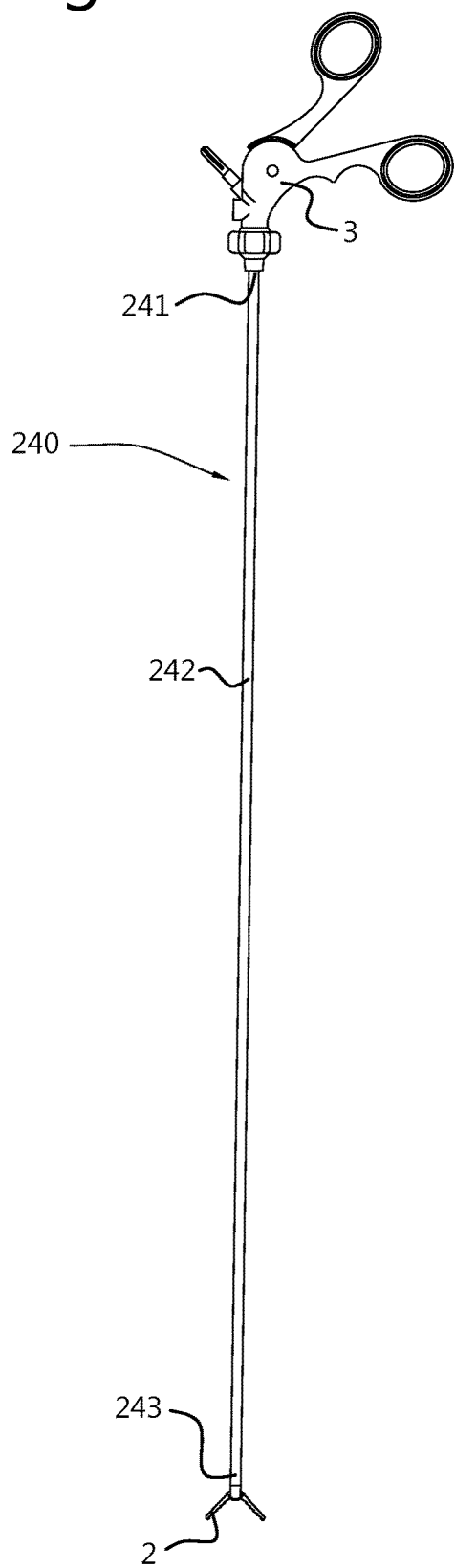
FIG. 2a shows a side view of a non-limiting embodiment of a rigid invasive instrument.
Figure 2B:
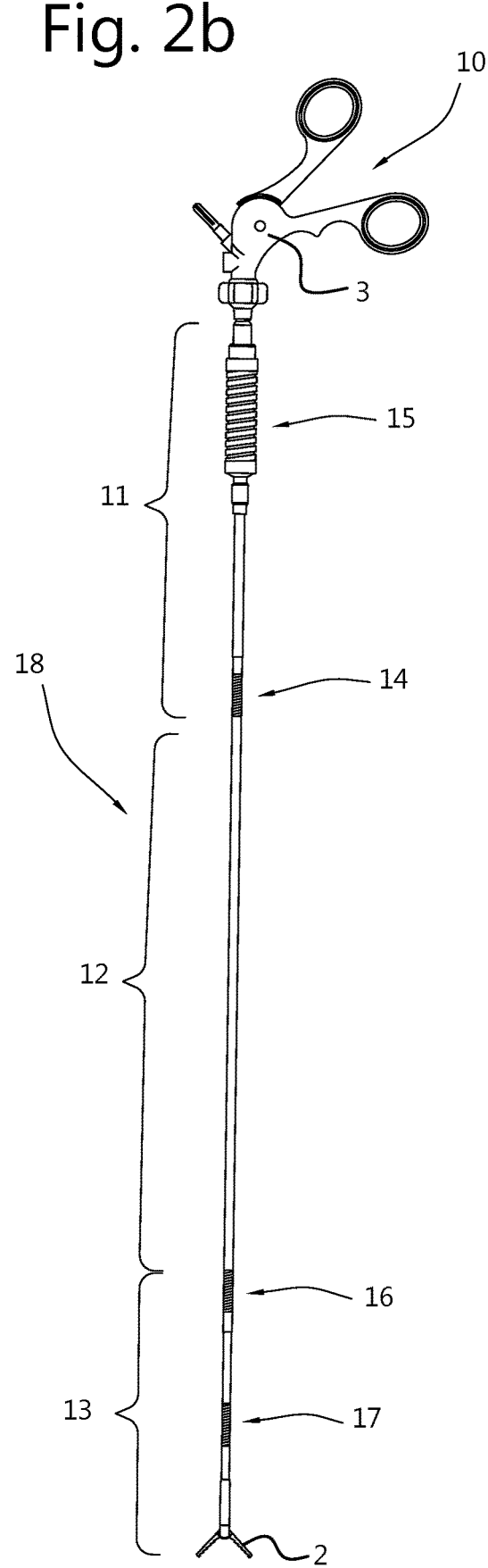
FIG. 2b shows a side view of a non-limiting embodiment of a steerable invasive instrument.
Figure 2C:
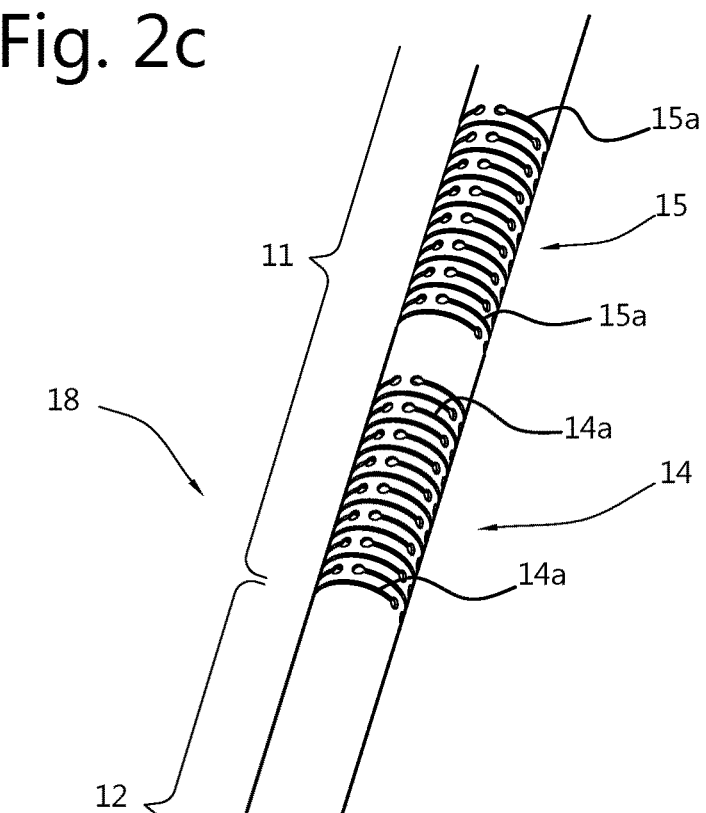

FIG. 2c provides a detailed perspective view of a non-limiting embodiment of the elongated tubular body of the steerable instrument.

Figure 2D:
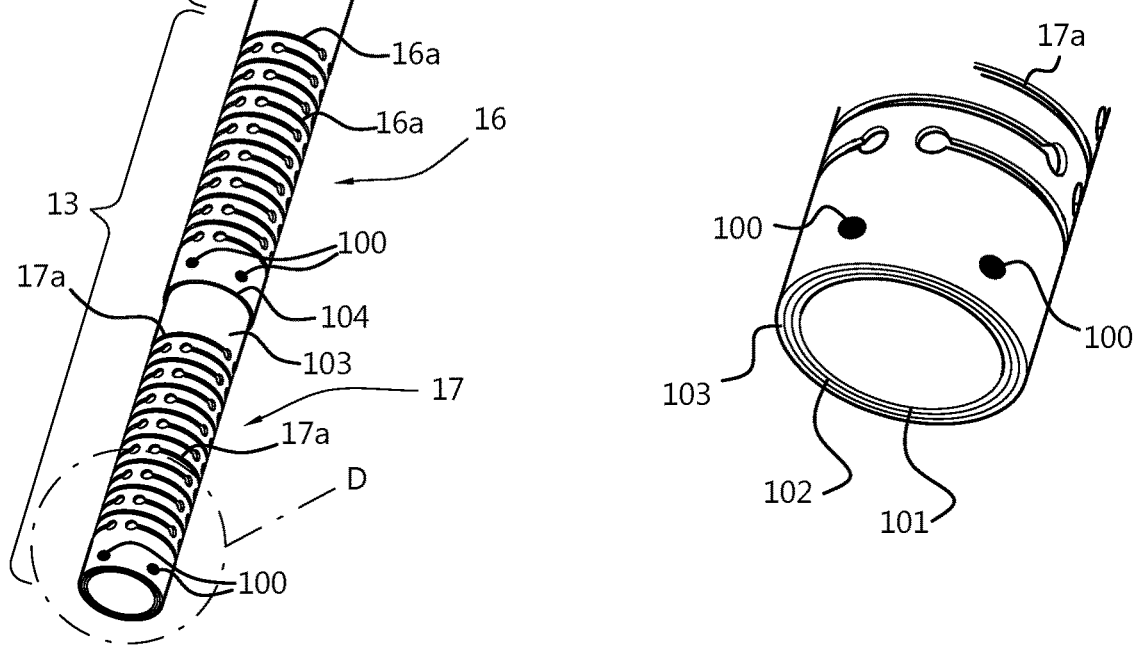

FIG. 2d provides a more detailed view of the distal end part of the elongated tubular body as shown in FIG. 2c.

Figure 2E:
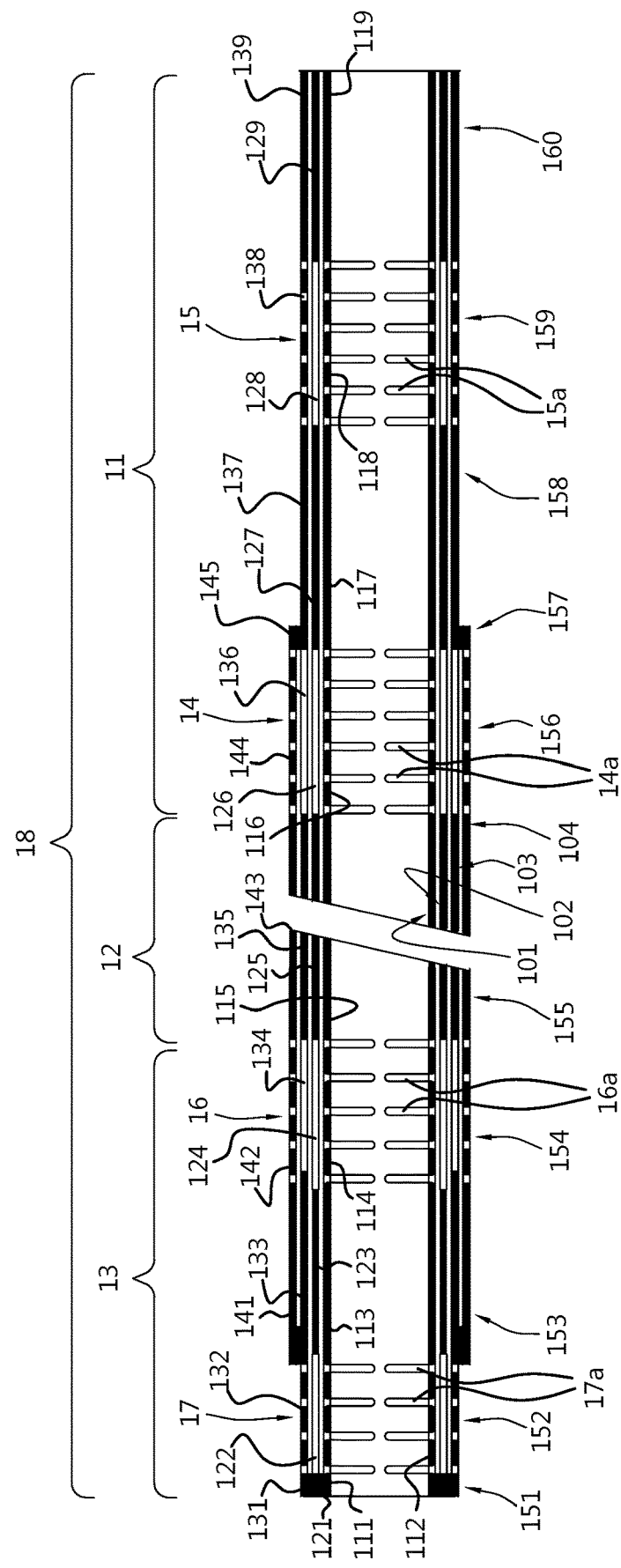

FIG. 2e shows a longitudinal cross-sectional view of the elongated tubular body of the steerable instrument as shown in FIG. 2c.

FIG. 2f shows a longitudinal cross-sectional view of the elongated tubular body of the steerable instrument as shown in FIG. 2c, wherein the first proximal and first distal flexible zones are bent, thereby illustrating the operation of the steering arrangement.

FIG. 2g shows a longitudinal cross-sectional view of the elongated tubular body of the steerable instrument as shown in FIG. 2f, wherein additionally the second proximal and second distal flexible zones are bent, thereby further illustrating the operation of the steering arrangement.

Figure 2H:
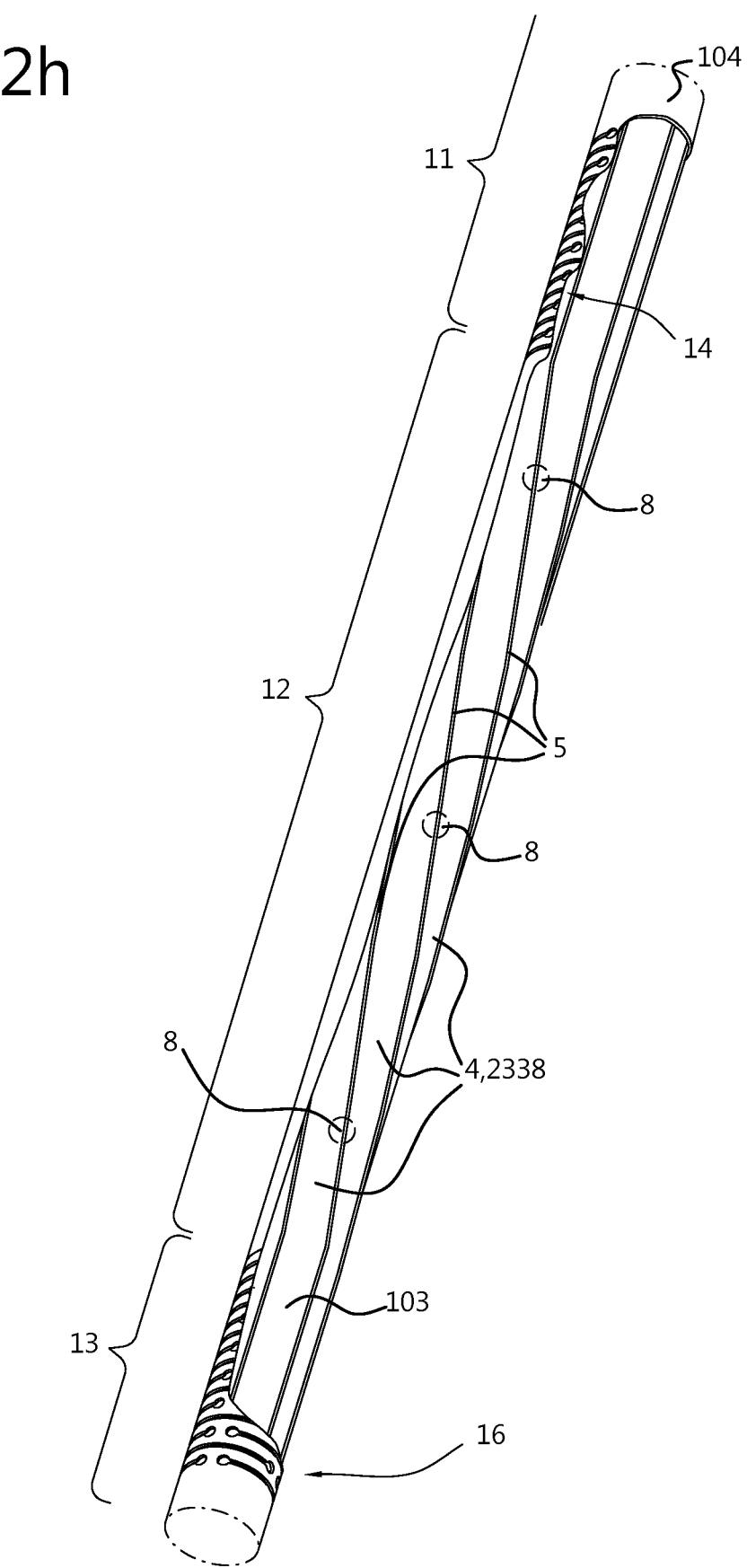

FIG. 2h shows a perspective view of a part of the elongated tubular body as shown in FIG. 2c, wherein the outer cylindrical element partially has been removed to show an exemplary embodiment of the longitudinal steering elements that have been obtained after providing longitudinal slits to the wall of an intermediate cylindrical element that interconnects the first proximal flexible zone and the first distal flexible zone of the elongated tubular body.

Figure 2I:
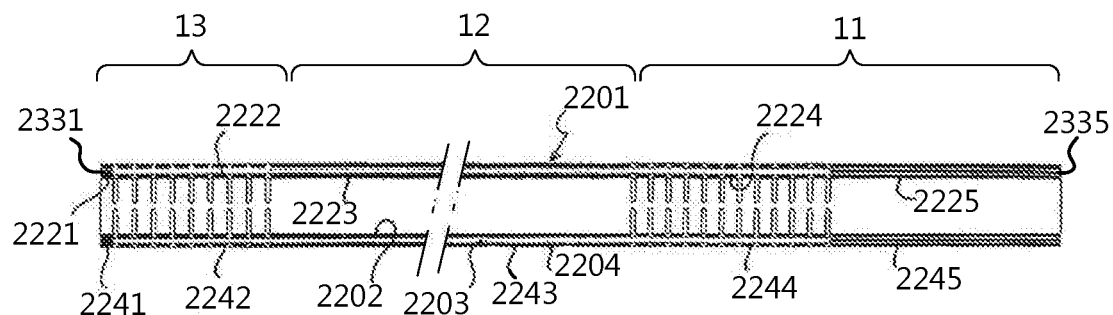

FIG. 2i shows a longitudinal cross-sectional view of an exemplary embodiment of a steerable instrument having one proximal and one distal flexible zone.

Figure 2J:
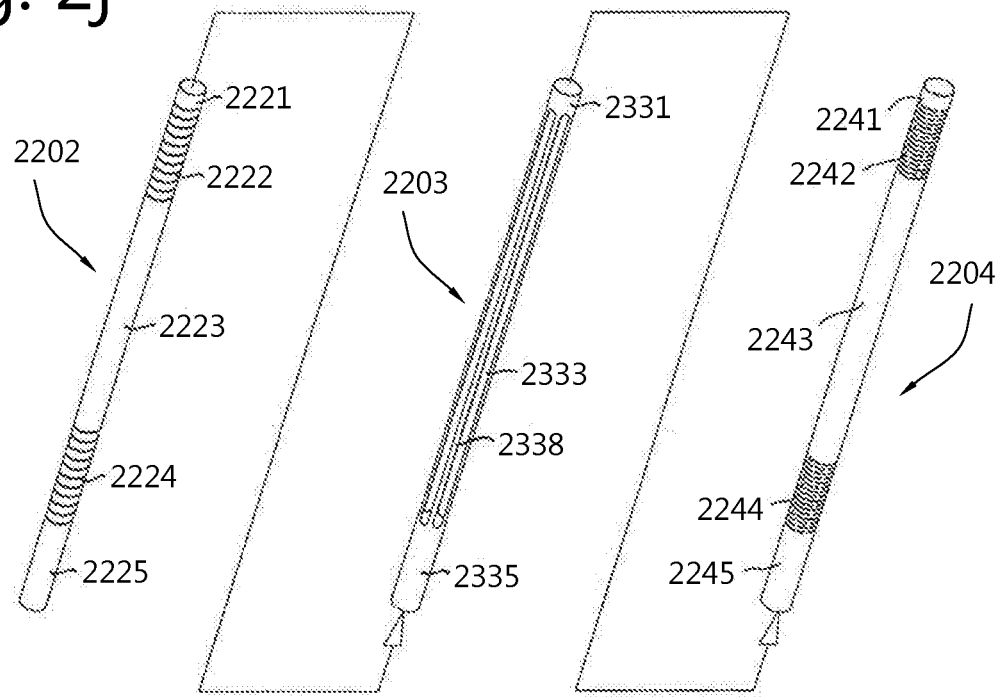

FIG. 2j shows a perspective exploded view of the three cylindrical elements of the steerable instrument shown in FIG. 2i.

Figure 2K:
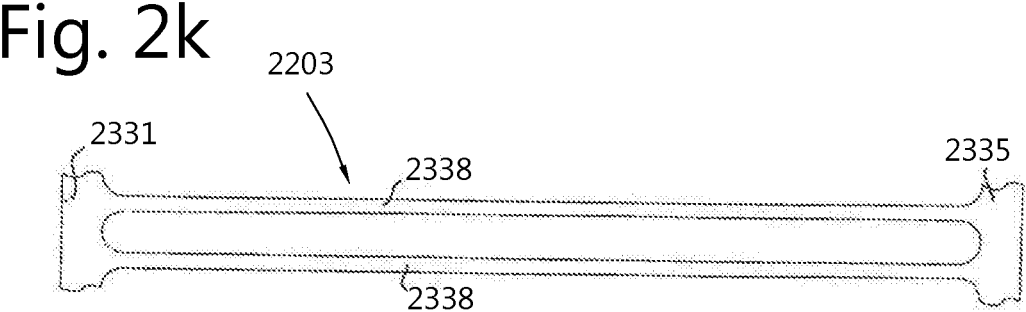

FIG. 2k shows a top view of an unrolled version of an exemplary embodiment of the intermediate cylindrical element of the steerable instrument shown in FIG. 2j. The intermediate cylindrical element can be formed by rolling the unrolled version into a cylindrical configuration and attaching adjacent sides of the rolled-up configuration by any known attaching means such as by a welding technique.

Figure 3A:
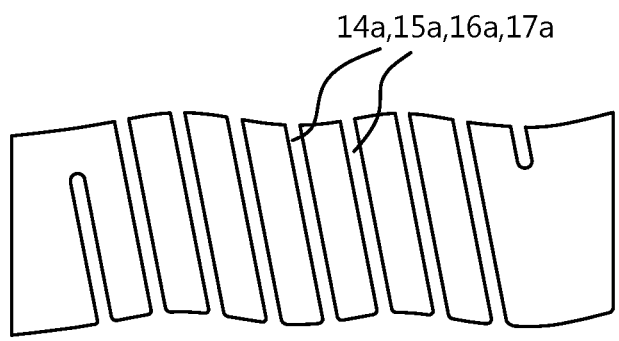
Figure 3B:
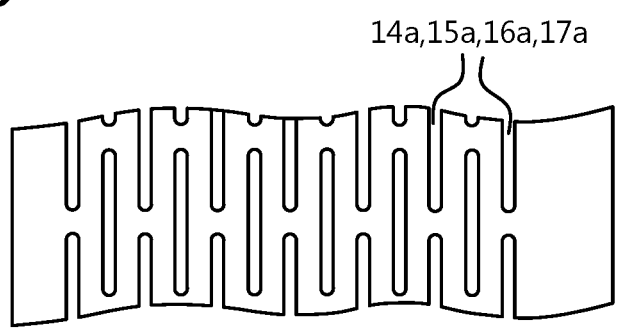
Figure 3C:
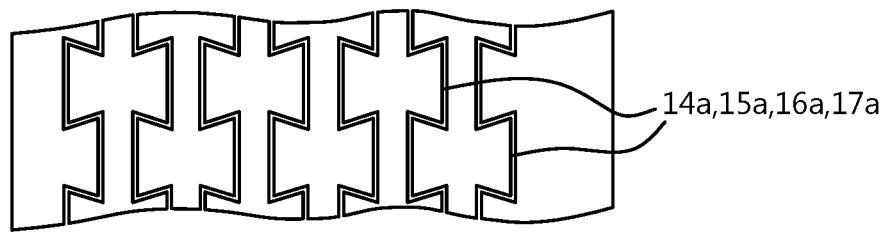

FIGS. 3a, 3b and 3c show schematic representation of unrolled views of embodiments of flexible proximal and distal parts of inner, outer and intermediate cylindrical elements.

Figure 4:
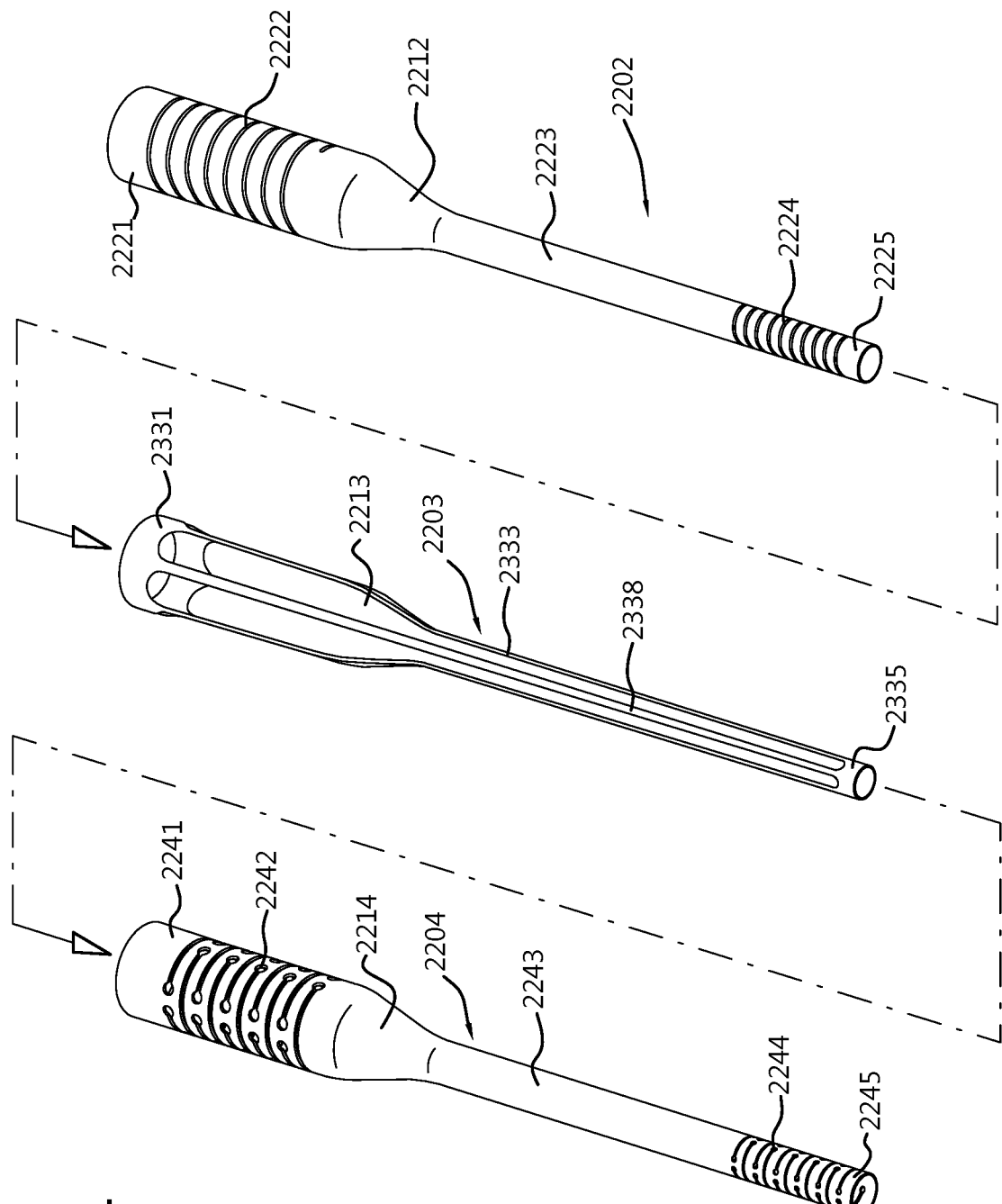

FIG. 4 shows a perspective exploded view of three cylindrical elements of a steerable tube analogous to the exploded view of FIG. 2j, but with a varying diameter of the cylindrical elements.

FIG. 5a shows a schematic cross-section of a first exemplary embodiment of a steerable instrument with cylindrical elements comparable as shown in FIGS. 3a, 3b and 3c. The proximal actuating portion of the cylindrical elements has a larger diameter compared to the distal handling end portion. A frusto-conical part schematically representing a cylindrical diameter adaptation section according to the invention has been incorporated in the intermediate rigid part that is arranged between the proximal end part and the distal end part to connect the parts of the elongated tubular body having different diameters.

FIG. 5b shows a schematic cross-section of a second exemplary embodiment of a steerable instrument in which a proximal actuation flexible zone of the actuating portion of the cylindrical elements as well as an intermediate rigid part that is arranged between said proximal actuation flexible zone and a distal actuation flexible zone have a larger diameter than the other parts of the elongated tubular body. A frusto-conical part is shown that schematically represents a diameter adaptation section according to the invention.

FIGS. 6-10 show consecutive manufacturing steps for producing a steerable instrument with an example of a diameter adaptation section according to the present invention.

Figure 11:
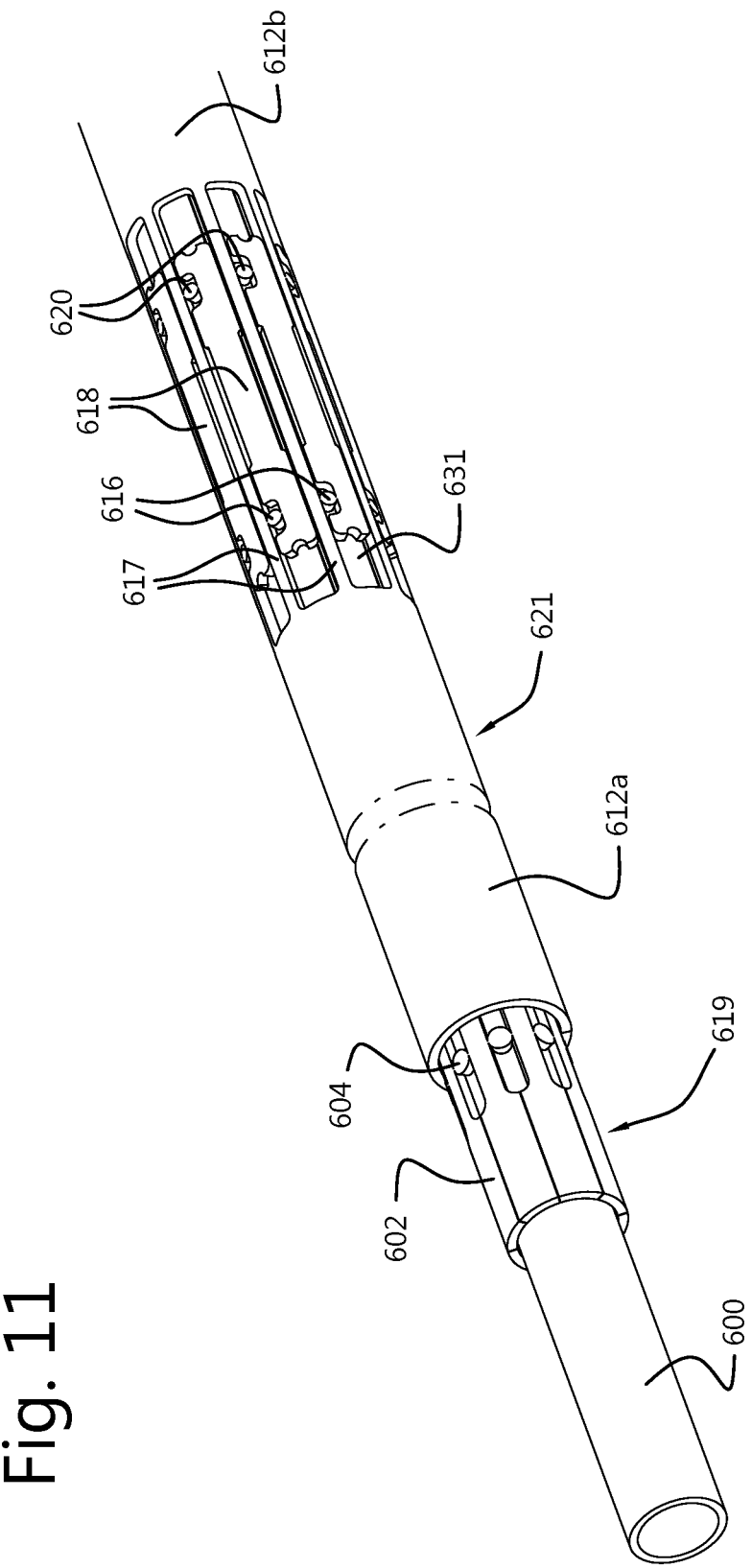

FIG. 11 shows an enlarged 3D view of a portion of the steerable instrument after the manufacturing step of FIG. 8.

Figure 12:
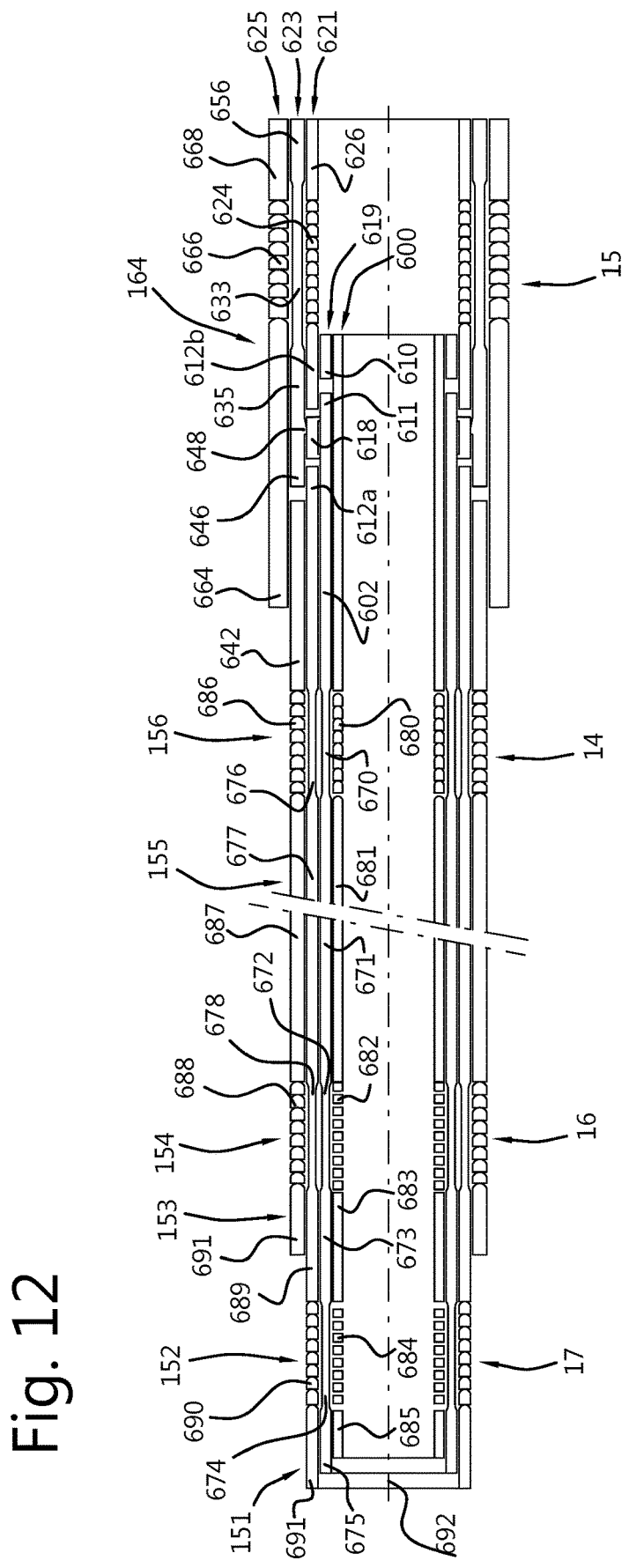

FIG. 12 shows a cross section of the steerable instrument in its assembled state.

Figure 13A:
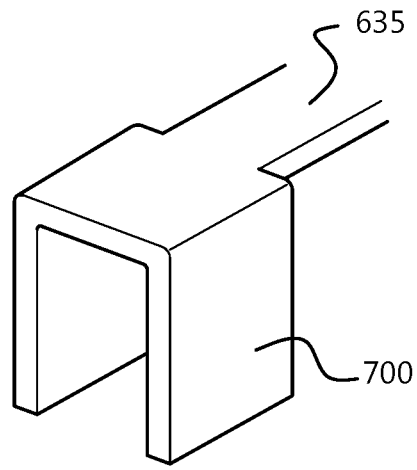
Figure 13B:
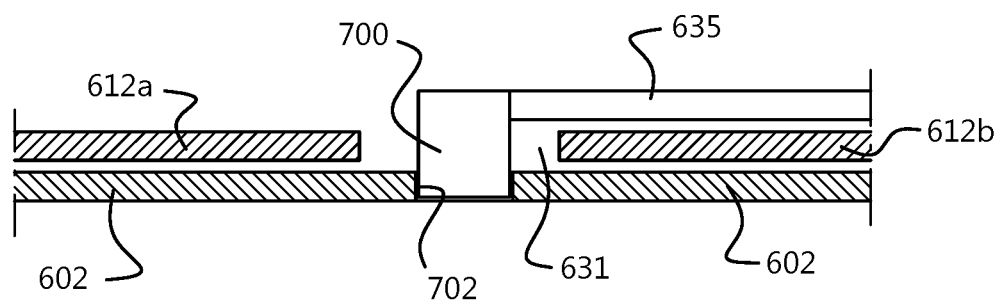

FIGS. 13a and 13b show an alternative implementation of a diameter adaptation section.

Figure 14A:
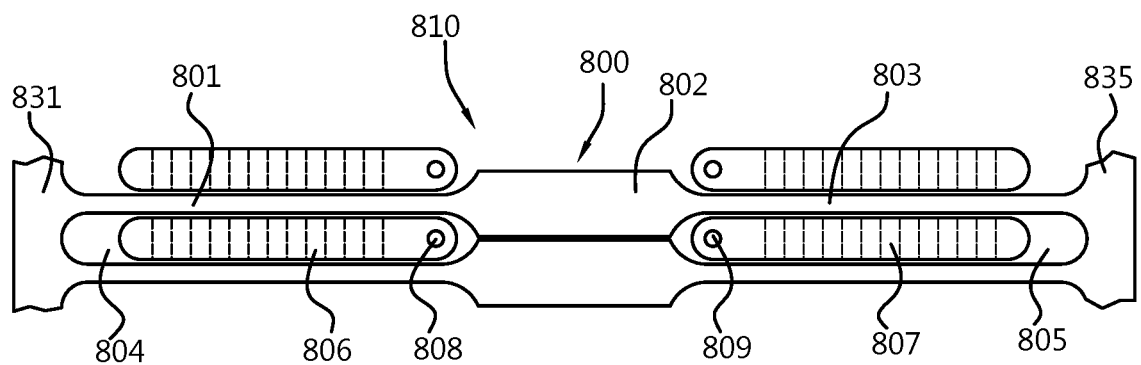
Figure 14B:
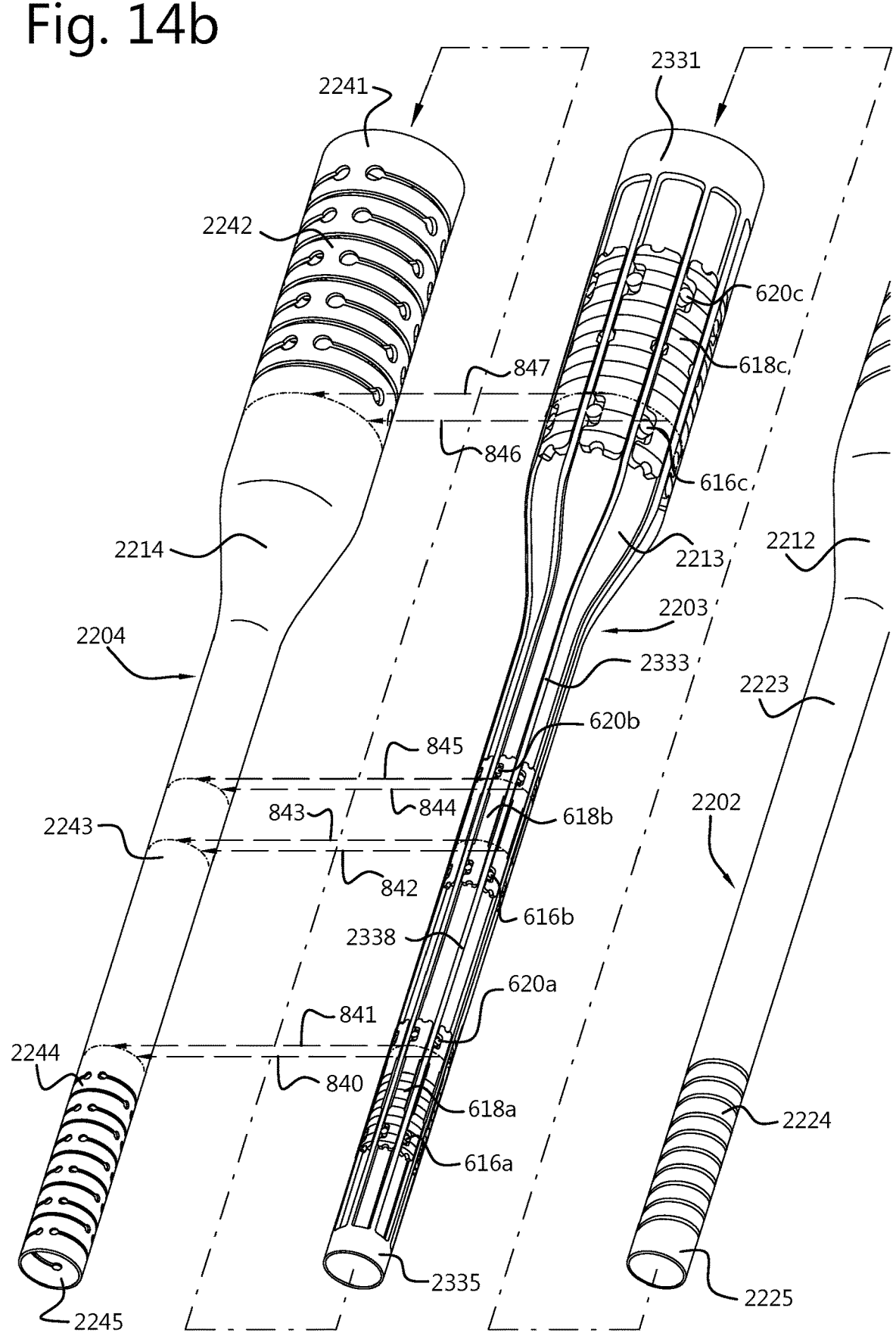

FIGS. 14a and 14b, respectively, show a design of a steerable instrument with spacers to keep portions of adjacent longitudinal elements at a certain distance from each other according to the prior art and to the invention, respectively.

Figure 1:
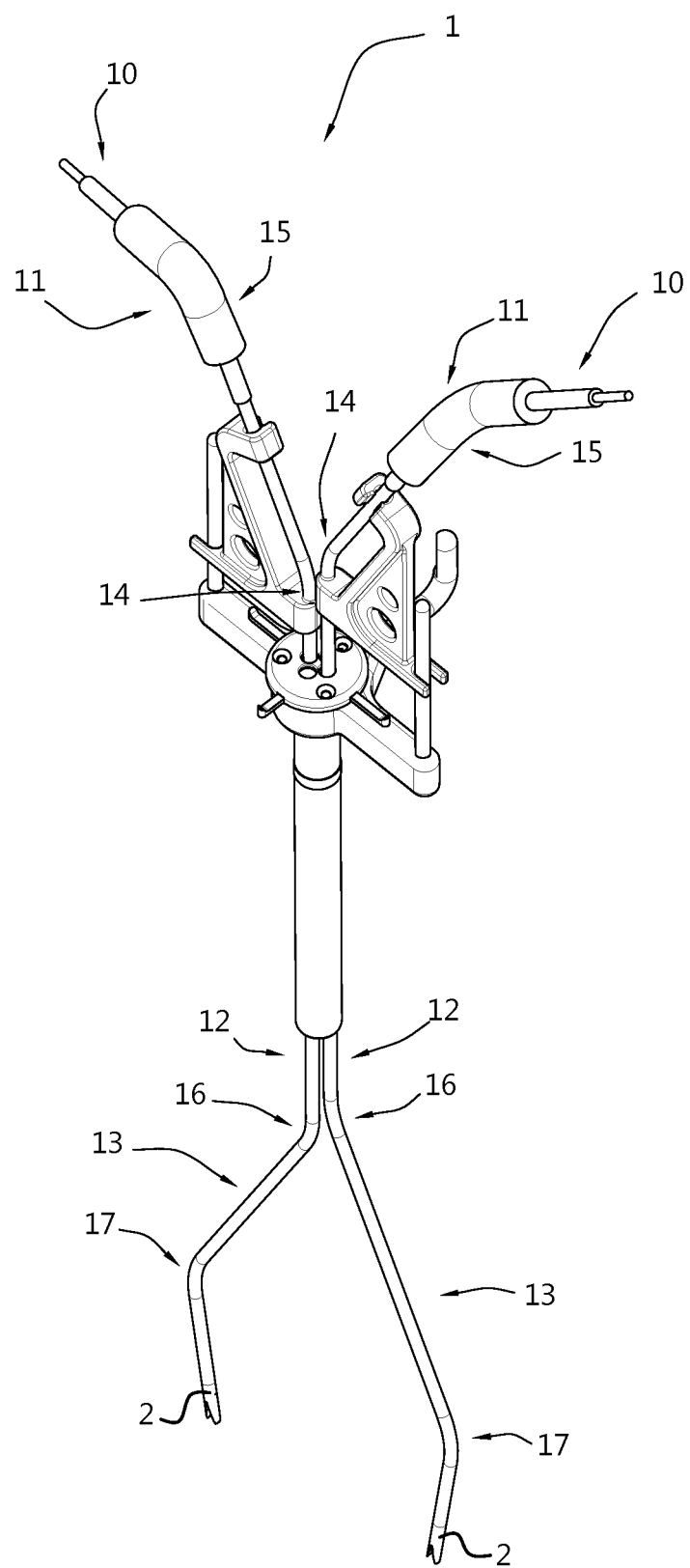
FIG. 1 shows a schematic perspective view of a non-limiting embodiment of an invasive instrument assembly having two steerable instruments.

FIG. 2a shows a side view of a non-limiting embodiment of a rigid invasive instrument 240 and FIG. 2b shows a non-limiting embodiment of a steerable invasive instrument 10. FIG. 1 shows a non-limiting embodiment of an invasive instrument assembly 1 having an introducer with two such steerable invasive instruments 10. Details of the non-limiting embodiment of the steerable invasive instruments 10 are explained in relation to FIGS. 2c to 2k.

The rigid invasive instrument 240 as shown in FIG. 2a comprises an elongated shaft 242 having a proximal end part 241 and a distal end part 243. At the distal end part 243 a tool 2, for example a forceps, is arranged. At the proximal end part 241 a handle 3 is arranged that is adapted for manipulating the tool 2, i.e. opening and closing the jaw of the forceps. To that effect, a control rod (not shown) is present within the elongated shaft 242, which rod connects the handle 3 with the tool 2. The rod can be moved by the handle 3 and the movement of the rod is translated into a predetermined movement of the tool 2, as is known to persons skilled in the art and need no further explanation here. Also, the shaft 242 may comprise conducting wires to allow a current to flow to a tool, e.g. to heat said tool in order to perform a heat treatment within a human or animal body.

FIG. 2b shows a side view of a steerable invasive instrument 10. The steerable instrument 10 comprises an elongated tubular body 18 having a proximal end part 11 including two actuation flexible zones 14, 15, a distal end part 13 including two distal flexible zones 16, 17, and a rigid intermediate part 12. The actuation flexible zones 14, 15 in the present embodiment are configured as flexible proximal zones, and will further be referred to as flexible proximal zones. At the distal end part 13 a tool, like a forceps 2 is arranged. At the proximal end part 11 a handle 3 is arranged that is adapted for opening and closing the jaw of the forceps 2.

FIG. 2c provides a detailed perspective view of the distal portion of the elongated tubular body 18 of the steerable instrument 10 and shows that the elongated tubular body 18 comprises of a number of co-axially arranged layers or cylindrical elements including an outer cylindrical element 104 that ends after the first distal flexible zone 16 at the distal end portion 13. The distal end portion 13 of the outer cylindrical element 104 is fixedly attached to the cylindrical element 103 located within and adjacent to the outer cylindrical element 104, e.g. by means of spot welding at welding spots 100. However, any other suitable attachment method can be used, including any mechanical snap fit connection or gluing by a suitable glue.

FIG. 2d provides a more detailed view of the distal end part 13 and shows that it includes three co-axially arranged layers or cylindrical elements being an inner cylindrical element 101, a first intermediate cylindrical element 102 and a second intermediate cylindrical element 103. The distal ends of inner cylindrical element 101, first intermediate cylindrical element 102 and second intermediate cylindrical element 103 are all three fixedly attached to one another. This may be done by means of spot welding at welding spots 100. However, any other suitable attachment method can be used, including any mechanical snap fit connection or gluing by a suitable glue. The points of attachment may be at the end edges of inner cylindrical element 101, first intermediate cylindrical element 102 and second intermediate cylindrical element 103, as shown in the figures. However, these points of attachment may also be located some distance away from these edges, be it, preferably, between the end edges and the locations of the flexible zone 17.

It will be clear to the skilled person that the elongated tubular body 18 as shown in FIG. 2c comprises four cylindrical elements in total. The elongated tubular body 18 according to the embodiment shown in FIG. 2c comprises two intermediate cylindrical elements 102 and 103 in which the steering members of the steering arrangement are arranged. The steering arrangement in the exemplary embodiment of the elongated tubular body 18 as shown in FIG. 2c comprises the two flexible zones 14, 15 at the proximal end part 11 of the elongated tubular body 18, the two flexible zones 16, 17 at the distal end part 13 of the elongated tubular body 18 and the steering members that are arranged between related flexible zones at the proximal 11 and distal 13 end parts. An exemplary actual arrangement of the steering members is shown in FIG. 2e, which provides a schematic longitudinal cross-sectional view of the exemplary embodiment of the elongated tubular body 18 as shown in FIG. 2c.

FIG. 2e shows the four layers or cylindrical elements mentioned above, i.e. the inner cylindrical element 101, the first intermediate cylindrical element 102, the second intermediate cylindrical element 103, and the outer cylindrical element 104.

The inner cylindrical element 101, as seen along its length from the distal end to the proximal end of the instrument, comprises a rigid ring 111, which is arranged at the distal end part 13 of the steerable instrument 10, a first flexible portion 112, a first intermediate rigid portion 113, a second flexible portion 114, a second intermediate rigid portion 115, a third flexible portion 116, a third intermediate rigid portion 117, a fourth flexible portion 118, and a rigid end portion 119, which is arranged at the proximal end portion 11 of the steerable instrument 10.

The first intermediate cylindrical element 102, as seen along its length from the distal end to the proximal end of the instrument, comprises a rigid ring 121, a first flexible portion 122, a first intermediate rigid portion 123, a second flexible portion 124, a second intermediate rigid portion 125, a third flexible portion 126, a third intermediate rigid portion 127, a fourth flexible portion 128, and a rigid end portion 129. The longitudinal dimensions of the rigid ring 121, the first flexible portion 122, the first intermediate rigid portion 123, the second flexible portion 124, the second intermediate rigid portion 125, the third flexible portion 126, the third intermediate rigid portion 127, the fourth flexible portion 128, and the rigid end portion 129 of the first intermediate element 102, respectively, are aligned with, and preferably approximately equal to the longitudinal dimensions of the rigid ring 111, the first flexible portion 112, the first intermediate rigid portion 113, the second flexible portion 114, the second intermediate rigid portion 115, the third flexible portion 116, the third intermediate rigid portion 117, the fourth flexible portion 118, and the rigid end portion 119 of the inner cylindrical element 101, respectively, and are coinciding with these portions as well. In this description "approximately equal" means that respective same dimensions are equal within a margin of less than 10%, preferably less than 5%.

The second intermediate cylindrical element 103, as seen along its length from the distal end to the proximal end of the instrument, comprises a first rigid ring 131, a first flexible portion 132, a second rigid ring 133, a second flexible portion 134, a first intermediate rigid portion 135, a first intermediate flexible portion 136, a second intermediate rigid portion 137, a second intermediate flexible portion 138, and a rigid end portion 139. The longitudinal dimensions of the first rigid ring 131, the first flexible portion 132 together with the second rigid ring 133 and the second flexible portion 134, the first intermediate rigid portion 135, the first intermediate flexible portion 136, the second intermediate rigid portion 137, the second intermediate flexible portion 138, and the rigid end portion 139 of the second intermediate cylinder 103, respectively, are aligned with, and preferably approximately equal to the longitudinal dimensions of the rigid ring 111, the first flexible portion 112, the first intermediate rigid portion 113, the second flexible portion 114, the second intermediate rigid portion 115, the third flexible portion 116, the third intermediate rigid portion 117, the fourth flexible portion 118, and the rigid end portion 119 of the first intermediate element 102, respectively, and are coinciding with these portions as well.

The outer cylindrical element 104, as seen along its length from the distal end to the proximal end of the instrument, comprises a first rigid ring 141, a first flexible portion 142, a first intermediate rigid portion 143, a second flexible portion 144, and a second rigid ring 145. The longitudinal dimensions of the first flexible portion 142, the first intermediate rigid portion 143 and the second flexible portion 144 of the outer cylindrical element 104, respectively, are aligned with, and preferably approximately equal to the longitudinal dimension of the second flexible portion 134, the first intermediate rigid portion 135 and the first intermediate flexible portion 136 of the second intermediate element 103, respectively, and are coinciding with these portions as well. The rigid ring 141 has approximately the same length as the rigid ring 133 and is fixedly attached thereto, e.g. by spot welding or gluing. Preferably, the rigid ring 145 overlaps with the second intermediate rigid portion 137 only over a length that is required to make an adequate fixed attachment between the rigid ring 145 and the second intermediate rigid portion 137, respectively, e.g. by spot welding or gluing. The rigid rings 111, 121 and 131 are attached to each other, e.g., by spot welding or gluing. This may be done at the end edges thereof but also at a distance of these end edges.

In an embodiment, the same may apply to the rigid end portions 119, 129 and 139, which can be attached together as well in a comparable manner. However, as will be explained hereinafter, the construction may be such that the diameter of the cylindrical elements at the proximal portion is larger, or smaller, with respect to the diameter at the distal portion. In such embodiment the construction at the proximal portion differs from the one shown in FIG. 2e. As a result of the increase or decrease in diameter an amplification or attenuation is achieved, i.e., the bending angle of a flexible zone at the distal portion will be larger or smaller than the bending angle of a corresponding flexible portion at the proximal portion. This will be further described below with reference to FIG. 4.

The inner and outer diameters of the cylindrical elements 101, 102, 103, and 104 are chosen in such a way at a same location along the elongated tubular body 18 that the outer diameter of inner cylindrical element 101 is slightly less than the inner diameter of the first intermediate cylindrical element 102, the outer diameter of the first intermediate cylindrical element 102 is slightly less than the inner diameter of the second intermediate cylindrical element 103 and the outer diameter of the second intermediate cylindrical element 103 is slightly less than the inner diameter of the outer cylindrical element 104, in such a way that a sliding movement of the adjacent cylindrical elements with respect to each other is possible. The dimensioning should be such that a sliding fit is provided between adjacent elements. A clearance between adjacent elements may generally be in the order of 0.02 to 0.1 mm, but depends on the specific application and material used. The clearance preferably is smaller than a wall thickness of the longitudinal elements to prevent an overlapping configuration thereof. Restricting the clearance to about 30% to 40% of the wall thickness of the longitudinal elements is generally sufficient.

As can be seen in FIG. 2e, flexible zone 14 of the proximal end part 11 is connected to the flexible zone 16 of the distal end part 13 by portions 134, 135 and 136, of the second intermediate cylindrical element 103, which form a first set of longitudinal steering members of the steering arrangement of the steerable instrument 10. Furthermore, flexible zone 15 of the proximal end part 11 is connected to the flexible zone 17 of the distal end part 13 by portions 122, 123, 124, 125, 126, 127, and 128 of the first intermediate cylindrical element 102, which form a second set of longitudinal steering members of the steering arrangement. The use of the construction as described above allows the steerable instrument 10 to be used for double bending. The working principle of this construction will be explained with respect to the examples shown in FIGS. 2f and 2g.

For the sake of convenience, as shown in FIGS. 2e, 2f and 2g, the different portions of the cylindrical elements 101, 102, 103, and 104 have been grouped into zones 151-160 that are defined as follows. Zone 151 comprises the rigid rings 111, 121, and 131. Zone 152 comprises the portions 112, 122, and 132. Zone 153 comprises the rigid rings 133 and 141 and the portions 113 and 123. Zone 154 comprises the portions 114, 124, 134 and 142. Zone 155 comprises the portions 115, 125, 135 and 143. Zone 156 comprises the portions 116, 126, 136 and 144. Zone 157 comprises the rigid ring 145 and the parts of the portions 117, 127, and 137 coinciding therewith. Zone 158 comprises the parts of the portions 117, 127, and 137 outside zone 157. Zone 159 comprises the portions 118, 128 and 138. Finally, zone 160 comprises the rigid end portions 119, 129 and 139.

In order to deflect at least a part of the distal end part 13 of the steerable instrument 10, it is possible to apply a bending force, in any radial direction, to zone 158. According to the examples shown in FIGS. 2*f* and 2*g*, zone 158 is bent downwards with respect to zone 155. Consequently, zone 156 is bent downwards. Because of the first set of steering members comprising portions 134, 135, and 136 of the second intermediate cylindrical element 103 that are arranged between the second intermediate rigid portion 137 and the second rigid ring 133, the downward bending of zone 156 is transferred by a longitudinal displacement of the first set of steering members into an upward bending of zone 154 with respect to zone 155. This is shown in both FIGS. 2*f* and 2*g*.

It is to be noted that the exemplary downward bending of zone 156, only results in the upward bending of zone 154 at the distal end of the instrument as shown in FIG. 2*f*. Bending of zone 152 as a result of the bending of zone 156 is prevented by zone 153 that is arranged between zones 152 and 154. When subsequently a bending force, in any radial direction, is applied to the zone 160, zone 159 is also bent. As shown in FIG. 2*g*, zone 160 is bent in an upward direction with respect to its position shown in FIG. 2*f*. Consequently, zone 159 is bent in an upward direction. Because of the second set of steering members comprising portions 122, 123, 124, 125, 126, 127 and 128 of the first intermediate cylindrical element 102 that are arranged between the rigid ring 121 and the rigid end portion 129, the upward bending of zone 159 is transferred by a longitudinal displacement of the second set of steering members into a downward bending of zone 152 with respect to its position shown in FIG. 2*f*.

FIG. 2*g* further shows that the initial bending of the instrument in zone 154 as shown in FIG. 2*f* will be maintained because this bending is only governed by the bending of zone 156, whereas the bending of zone 152 is only governed by the bending of zone 159 as described above. Due to the fact that zones 152 and 154 are bendable independently with respect to each other, it is possible to give the distal end part 13 of the steerable instrument 10 a position and longitudinal axis direction that are independent from each other. In particular the distal end part 13 can assume an advantageous S-like shape. The skilled person will appreciate that the capability to independently bend zones 152 and 154 with respect to each other, significantly enhances the maneuverability of the distal end part 13 and therefore of the steerable instrument 10 as a whole.

Obviously, it is possible to vary the lengths of the flexible portions shown in FIGS. 2*e* to 2*g* as to accommodate specific requirements with regard to bending radii and total lengths of the distal end part 13 and the proximal end part 11 of the steerable instrument 10 or to accommodate amplification or attenuation ratios between bending of at least a part of the proximal end part 11 and at least a part of the distal end part 13.

The steering members comprise one or more sets of longitudinal elements that form integral parts of the one or more intermediate cylindrical elements 102, 103. Preferably, the longitudinal elements comprise remaining parts of the wall of an intermediate cylindrical element 102, 103 after the wall of the intermediate cylindrical element 102, 103 has been provided with longitudinal slits that define the remaining longitudinal steering elements.

Further details regarding the fabrication of the latter longitudinal steering elements are provided with reference to FIGS. 2*i* to 2*k* regarding an exemplary embodiment of a steerable instrument that comprises only one flexible zone at both its proximal 11 and distal end 13 parts.

FIG. 2*i* shows a longitudinal cross-section of a steerable instrument 2201 comprising three co-axially arranged cylindrical elements, i.e. inner cylindrical element 2202, intermediate cylindrical element 2203 and outer cylindrical element 2204. Suitable materials to be used for making the cylindrical elements 2202, 2203, and 2204 include stainless steel, cobalt-chromium, shape memory alloy such as Nitinol®, plastic, polymer, composites or other cuttable material. Alternatively, the cylindrical elements can be made by a 3D printing process.

The inner cylindrical element 2202 comprises a first rigid end part 2221, which is located at the distal end part 13 of the instrument 2201, a first flexible part 2222, an intermediate rigid part 2223, a second flexible part 2224 and a second rigid end part 2225, which is located at the proximal end part 11 of the instrument 2201.

The outer cylindrical element 2204 also comprises a first rigid end part 2241, a first flexible part 2242, an intermediate rigid part 2243, a second flexible part 2244 and a second rigid end part 2245. The lengths of the different parts of the cylindrical elements 2202 and 2204 are substantially the same so that when the inner cylindrical element 2202 is inserted into the outer cylindrical element 2204, the different parts are positioned against each other.

The intermediate cylindrical element 2203 also has a first rigid end part 2331 and a second rigid end part 2335 which in the assembled condition are located between the corresponding rigid parts 2221, 2241 and 2225, 2245 respectively of the two other cylindrical elements 2202, 2204. The intermediate part 2333 of the intermediate cylindrical element 2203 comprises three or more separate longitudinal elements which can have different forms and shapes as will be explained below. After assembly of the three cylindrical elements 2202, 2203 and 2204 whereby the element 2202 is inserted in the element 2203 and the two combined elements 2202, 2203 are inserted into the element 2204, at least the first rigid end part 2221 of the inner cylindrical element 2202, the first rigid end part 2331 of the intermediate cylindrical element 2203 and the first rigid end part 2241 of the outer cylindrical element 2204 at the distal end of the instrument are attached to each other. In the embodiment shown in FIGS. 2*i* and 2*j*, also the second rigid end part 2225 of the inner cylindrical element 2202, the second rigid end part 2335 of the intermediate cylindrical element 2203 and the second rigid end part 2245 of the outer cylindrical element 2204 at the proximal end of the instrument are attached to each other such that the three cylindrical elements 2202, 2203, 2204 form one integral unit.

In the embodiment shown in FIG. 2*j* the intermediate part 2333 of intermediate cylindrical element 2203 comprises a number of longitudinal elements 2338 with a uniform cross-section so that the intermediate part 2333 has the general shape and form as shown in the unrolled condition of the intermediate cylindrical element 2203 in FIG. 2*k*. From FIG. 2*k* it also becomes clear that the intermediate part 2333 is formed by a number of over the circumference of the intermediate cylindrical part 2203 equally spaced parallel longitudinal elements 2338. Advantageously, the number of longitudinal elements 2338 is at least three, so that the instrument 2201 becomes fully controllable in any direction, but any higher number is possible as well. Preferably, the number of longitudinal elements 2338 is 6 or 8.

The production of such an intermediate part is most conveniently done by injection moulding or plating techniques or starting from a cylindrical tube with the desired inner and outer diameters and removing parts of the wall of the cylindrical tube required to end up with the desired shape of the intermediate cylindrical element 2203. However, alternatively, any 3D printing method can be used.

The removal of material can be done by means of different techniques such as laser cutting, photochemical etching, deep pressing, conventional chipping techniques such as drilling or milling, high pressure water jet cutting systems or any suitable material removing process available. Preferably, laser cutting is used as this allows for a very accurate and clean removal of material under reasonable economic conditions. The above mentioned processes are convenient ways as the member 2203 can be made so to say in one process, without requiring additional steps for connecting the different parts of the intermediate cylindrical element as required in the conventional instruments, where conventional steering cables must be connected in some way to the end parts. The same type of technology can be used for producing the inner and outer cylindrical elements 2202 and 2204 with their respective flexible parts 2222, 2224, 2242 and 2244.

FIG. 2h shows an exemplary embodiment of longitudinal (steering) elements 4 that have been obtained after providing longitudinal slits 5 to the wall of the second intermediate cylindrical element 103 that interconnects proximal flexible zone 14 and distal flexible zone 16 as described above. I.e., longitudinal steering elements 4 are, at least in part, spiraling about a longitudinal axis of the instrument such that an end portion of a respective steering element 4 at the proximal portion of the instrument is arranged at another angular orientation about the longitudinal axis than an end portion of the same longitudinal steering element 4 at the distal portion of the instrument. Were the longitudinal steering elements 4 arranged in a linear orientation, than a bending of the instrument at the proximal portion in a certain plane would result in a bending of the instrument at the distal portion in the same plane but in a 180 degrees opposite direction. This spiral construction of the longitudinal steering elements 4 allows for the effect that bending of the instrument at the proximal portion in a certain plane may result in a bending of the instrument at the distal portion in another plane, or in the same plane in the same direction. A preferred spiral construction is such that the end portion of a respective steering element 4 at the proximal portion of the instrument is arranged at an angularly shifted orientation of 180 degrees about the longitudinal axis relative to the end portion of the same longitudinal steering element 4 at the distal portion of the instrument. However, e.g. any other angularly shifted orientation, e.g. 90 degrees, is within the scope of this document. The slits are dimensioned such that movement of a longitudinal element is guided by adjacent longitudinal elements when provided in place in a steerable instrument.

The flexible portions 112, 132, 114, 142, 116, 144, 118, and 138 as shown in FIG. 2e, as well as the flexible parts 2222, 2224, 2242, and 2244 shown in FIGS. 2i and 2j can be obtained by the methods described in European patent application 08 004 373.0 filed on 10 Mar. 2008, page 5, lines 15-26, but any other suitable process can be used to make flexible portions.

Such flexible parts may have a structure as shown in FIGS. 2c and 2d. I.e., the flexibility may be obtained by a plurality of slits 14a, 15a, 16a, 17a. E.g., two circumferential slits may be provided in a cylindrical element along a same circumferential line where both slits are located at a certain distance from one another. A plurality of identical sets of circumferential slits 14a, 15a, 16a, 17a is provided at a plurality of distances in the longitudinal direction of the instrument, where consecutive sets are arranged at an angularly rotated position, e.g. each time 90 degrees rotated. In such an arrangement, all parts of the cylindrical element are still connected to each other.

FIGS. 3a, 3b and 3c show alternative manners of how such flexibility in part can be obtained. FIG. 3a shows a schematic representation of a flat rolled-out flexible proximal or distal cylindrical zone. The intermediate cylindrical elements are then made by rolling-up the flat element and attaching the side edges together in any suitable fashion that is known as such, such as by a welding technique. In the embodiment shown in FIG. 3a, the part of the cylindrical tube to become flexible has been provided with slits 14a, 15a, 16a, 17a extending in a helical manner over the length of the flexible zone. The flexibility can be controlled by the number of slits and/or the angle of the slits with respect to the axial direction of the cylindrical element. In the embodiment of FIG. 3b the part of the cylindrical tube to become flexible has been provided with a number of short slits 14a, 15a, 16a, 17a. The slits can be divided into groups, the slits in each group being located in the same line extending perpendicular to the axis of the cylindrical element. The slits of two neighboring groups are offset. In the embodiment of FIG. 3c the part of the cylindrical tube to become flexible has been provided by making slits 14a, 15a, 16a, 17a producing a number of swallow's tails between the slits, which fit into each other as shown. It will be obvious that other systems of providing a flexible zone in a cylindrical tube wall may be used as well. More specifically it is possible to use combinations of the systems shown above. However, any other suitable flexible construction may be used instead. For instance, any of the flexible constructions shown and described in EP 0 764 423 A and EP 0 782 836 A may be used as well.

Furthermore, if the portions 122, 123, 124, 125, 126, 127, and 128 of the first intermediate cylindrical element 102 and the portions 134, 135, and 136 of the second intermediate cylindrical element 103 that respectively form the first and second set of longitudinal steering members, as shown in FIG. 2e, are implemented as longitudinal steering elements 4 as shown in FIG. 2h, the fabrication methods described above can be used. The same applies to the longitudinal elements 2338 of FIGS. 2j and 2k. Moreover, any embodiment described in EP 2 762 058 A can be used according to the invention.

Otherwise, the longitudinal elements 4, 2338 can also be obtained by any other technique known in the art such as for example described in EP 1 708 609 A. The only restriction with respect to the construction of the longitudinal elements used in these portions is that the total flexibility of the instrument in these locations where the flexible portions coincide must be maintained.

The different co-axially arranged layers or cylindrical elements 101, 102, 103, 104, 2202, 2203 and 2204 as described above in relation to the exemplary embodiments of the steerable instruments shown in FIGS. 2e and 2i, respectively, may be produced by any of the known methods, provided that they are suitable to make a multilayer system. A multilayer system is to be understood as being a steerable instrument that comprises at least two separate sets of longitudinal elements 4, 2338 for transferring the movement of the proximal end part to the distal end part. The assembly of the different cylindrical elements can be realized in the same way as well. Preferred methods of producing the different cylindrical elements have been described in the above mentioned EP 2 762 058 A which is hereby incorporated by reference in its entirety.

In the above embodiments, the proximal portions and distal portions are constructed in a similar way. However, that need not be the case always as will be explained now.

E.g., the proximal portion may have a wider diameter as shown in FIG. 4, which shows a special embodiment of an instrument according to the invention. The inner cylindrical element 2202 is composed of a first rigid end part 2225, a first flexible part 2224, an intermediate rigid part 2223, a second flexible part 2222 and a second rigid end part 2221 which is normally used as the operating part of the instrument in that it serves to steer the other end of the unit. The outer cylindrical element 2204 is in the same way composed of a first rigid part 2245, a first flexible part 2244, an intermediate rigid part 2243, a second flexible part 2242 and a second rigid part 2241. The intermediate cylindrical element 2203 also has a first rigid end part 2335 and a second rigid end part 2331 which in the assembled condition are located between the corresponding rigid parts 2225, 2245 and 2221, 2241, respectively, of the two other cylindrical elements 2202, 2204. In the embodiment shown the longitudinal elements 2338 are of the type shown in FIG. 2j, but it will be obvious that any other type described above may be used as well. So far the construction is comparable to the instruments described above. The main difference with respect to the above embodiments is the use of a different set of diameters for some parts of the instrument. In the embodiment shown in FIG. 4 the parts 2222, 2221, 2331, 2242 and 2241 have a larger diameter than the other parts. In the parts 2223, 2333 and 2243 frusto-conical portions 2212, 2213, 2214 have been made in order to connect the small diameter parts with the large diameter parts. As shown in FIG. 4 the different parts can easily be assembled by inserting one into the other. The main reason, however, to have such an instrument with different diameters is that by using an operating part with a larger diameter, the movement of the other end is amplified, whereas if a smaller diameter is used the movement of the other end is attenuated. Dependent of the application and its requirements larger diameters can be used to have the amplified movement or smaller diameters can be used to attenuate the movement and increase maneuverability accuracy of the handling head.

Such widening of the instrument with increasing diameter towards the proximal portions can also be applied in an instrument with more than two bendable portions, as shown in FIGS. 5a and 5b.

In FIG. 5a there is shown a first exemplary embodiment of a steerable instrument according to the invention having four layers and as such the instrument is comparable to the instrument of FIG. 2e but the distal actuation flexible zone 156 and the proximal actuation flexible zone 159 of the proximal end part of the instrument have a larger diameter compared to the respective corresponding distal flexible zones 154 and 152 of the distal end part of the instrument. In the zone 155 a frusto-conical part has been incorporated that schematically represents a cylindrical diameter adaptation section 162 of a steerable instrument according to the invention. The cylindrical diameter adaptation section 162 in the context of this invention occupies at least a distance in an axial or longitudinal direction of the elongated tubular body over which the longitudinal elements change from a second diameter at a first side of the cylindrical diameter adaptation section to a third diameter at a second side of the cylindrical diameter adaptation section. As a result of the larger diameter of the proximal actuation flexible zone 156 and the proximal actuation flexible zone 159 of the proximal end part, the flexion of the respective corresponding distal flexible zones 154 and 152 will be amplified upon bending, thereby amplifying the flexion of the handling head. It is also possible to work in the opposite direction with distal flexible zones 154 and 152 having a larger diameter than the proximal actuation flexible zones 156 and 159, whereby the degree of flexion is attenuated, thereby improving accuracy of movement of the handling head.

FIG. 5b shows a schematic cross-section of a second exemplary embodiment of a steerable instrument according to the invention in which a proximal actuation flexible zone 159 of the actuating portion of the cylindrical elements as well as an intermediate rigid zone 158, that is arranged between said proximal actuation flexible zone 159 and a proximal actuation flexible zone 156, have a larger diameter than the other parts of the elongated tubular body. A frusto-conical part schematically representing a cylindrical diameter adaptation section 164 of a steerable instrument according to the invention has been incorporated in zone 158. The cylindrical diameter adaptation section 164 in the context of this invention extends at least along distance in an axial or longitudinal direction of the elongated tubular body over which the longitudinal elements change from a second diameter at a first side of the cylindrical diameter adaptation section to a third diameter at a second side of the cylindrical diameter adaptation section. It will be clear to the skilled person that only the flexion of the corresponding distal flexible zone 152 will be amplified upon bending of the corresponding proximal actuation flexible zone 159 of the proximal end part. The degree of flexion of the distal flexible zone 154 will in principle be the same as the degree of flexion of the corresponding proximal actuation flexible zone 156, because of the fact that the intermediate cylindrical element, which comprises the longitudinal elements that are configured and arranged to transfer the flexion of the proximal actuation flexible zone 156 to the corresponding distal flexible zone 154, has the same diameter in these zones. In practice there may be slight differences between these degrees of flexion due to stretching of the longitudinal elements.

FIGS. 6-13b show how an increasing or decreasing diameter of a radius of a flexible actuation zone can be implemented and manufactured. I.e., FIGS. 6-10 show consecutive manufacturing actions performed to make a diameter adaptation section of a steerable instrument having five cylindrical elements inserted into one another (any other suitable number than five can, of course be used).

FIG. 6 shows an inner protective cylindrical element 600 having two opposing ends 601, 603. End 601 will be called the distal end, here, whereas end 603 will be called the proximal end. However, that could in practice be the other way around. The inner protective cylindrical element 600 is, preferably, a single cylindrical tube of any suitable material like stainless steel, cobalt-chromium, shape memory alloy such as Nitinol®, plastic, polymer, composites or other cuttable material. Alternatively, the inner protective cylindrical element 600 can be made by a 3D printing process. The thickness of that tube depends on its application. For medical applications the thickness may be in a range of 0.1-2.0 mm, preferably 0.1-1.0 mm, more preferably 0.1-0.5 mm, and most preferably 0.2-0.4 mm. The diameter of the inner protective cylindrical element 600 depends on its application. For medical applications the diameter may be in a range of 0.5-20 mm, preferably 0.5-10 mm, more preferably 0.5-6 mm.

FIG. 7 shows the inner protective cylindrical element 600 inserted into an intermediate cylindrical element 619. The intermediate cylindrical element 619 is provided with slits 605 which define adjacent longitudinal elements 602. As will become clear hereinafter, those longitudinal elements 602 can be used as pushing/pulling wires in the assembled state of the steerable instrument. The slits 605 can be made by laser cutting and have a width, preferably, in a range of 5-50 µm, more preferably 15-30 µm.

At end 615, i.e. the proximal end of the steerable instrument, the intermediate cylindrical element 619 comprises a rigid, ring-shaped element 610. The rigid, ring-shaped element 610 is attached to a set of finger-shaped elements 608. Preferably, the number of finger-shaped elements 608 equals the number of longitudinal elements 602.

Preferably, each longitudinal element 602, at the same end as rigid, ring-shaped element 610 is provided with one or more finger-shaped elements 611, each one being located between two adjacent finger-shaped elements 608.

Preferably, the intermediate cylindrical element 619 is made from a single cylindrical tube of any suitable material that may be the same material as the one from inner protective cylindrical element 600. The thickness of that tube depends on its application. For medical applications the thickness may be in a range of 0.1-2.0 mm, preferably 0.1-1.0 mm, more preferably 0.1-0.5 mm, and most preferably 0.2-0.4 mm. Intermediate cylindrical element 619 has a slightly larger diameter than inner protective cylindrical element 600, such that when inner protective cylindrical element 600 is inserted into intermediate cylindrical element 619, there is a clearance between them in a range of e.g. 0.02 to 0.1 mm. The diameter of the intermediate cylindrical element 619 depends on its application. For medical applications the diameter may be in a range of 0.5-20 mm, preferably 0.5-10 mm, more preferably 0.5-6 mm.

As explained above, the longitudinal elements 605 can then be made by laser cutting the cylindrical tube such as to render the slits 605, and thus, the longitudinal elements 602. If the slits 605 would be present along the entire length of the intermediate cylindrical elements 602 directly after the cutting process, it would be difficult to keep them together during the manufacturing process of the steerable instrument. Therefore, the cutting process is arranged such that after the cutting process is finished, at the end of the intermediate cylindrical element 619 opposing end 615 (or at any other desired location) adjacent longitudinal elements 602 are connected by so-called "break islands" 604.

These break islands 604 are, at two opposing ends, attached to two adjacent longitudinal elements 602. The break islands 604 are shown to have a circular shape and to be attached to adjacent longitudinal elements 602 by means of thin flexible bridges. In use, when the longitudinal elements 602 are used to control deflection of flexible portions of the steerable instrument, adjacent longitudinal elements 602 move relative to one another in the longitudinal direction of the steerable instrument. By this movement, at least one of the attachments of the break islands 604 to the adjacent longitudinal elements 602 will break such that the adjacent longitudinal elements 602 can move freely in the longitudinal direction. Such movement can be postponed until the steerable instrument has reached its assembled state. This greatly facilitates the manufacturing process of the steerable instrument since all adjacent longitudinal elements 602 can be kept together in a position such that, together, they still form their original cylindrical shape as long as possible.

Manufacturing of a steerable instrument while using break islands 604 can be summarized as follows: Such a steerable instrument comprises at least an elongated tubular body having a proximal end part, a distal end part and an intermediate part between the proximal and distal end parts, the proximal end part having at least one actuation proximal zone, the distal end part having at least one flexible distal zone, and the elongated tubular body being configured such that a movement of an actuation proximal zone is transferred to a corresponding flexible distal zone for a corresponding movement thereof. The elongated tubular body comprises an inner cylindrical element, an outer cylindrical element and at least one intermediate cylindrical element having longitudinal elements and provided between the inner and outer cylindrical elements, the inner, outer and intermediate cylindrical elements being coupled such that movement of an actuation proximal zone is transferred by the longitudinal elements of one of the intermediate cylindrical elements to a corresponding flexible distal zone.

The manufacturing actions can be summarized as follows:
providing the inner and outer cylindrical elements;
providing an intermediate cylindrical element such that adjacent longitudinal elements are attached to one another at one or more positions by one or more attachments distributed along a length of the longitudinal elements arranged to allow relative movement of the longitudinal elements with respect to one another in a longitudinal direction of the longitudinal elements, and so as to restrict movement of longitudinal elements in a radial direction of the intermediate cylindrical element; and
incorporating the intermediate cylindrical element between the inner and outer cylindrical elements,
wherein the one or more attachments are releasable attachments and the method comprises releasing said releasable attachments during said manufacturing.

Preferably, the steerable instrument is manufactured at to such a state that the intermediate cylinder with the longitudinal elements is inserted between a protective inner cylindrical element and a protective outer cylindrical element before the longitudinal elements are moved relative to one another such that the break islands will break off. Then, after these break islands have been broken off adjacent longitudinal elements keep their respective locations on a virtual cylinder between the protective inner and outer cylindrical elements.

A break island 604 is a fracture element which can be defined as follows. Each fracture element is configured and arranged to fracture when adjacent longitudinal elements 602 to which each such fracture element is attached are moved in a longitudinal direction relative to one another such as to develop an actual fracture element stress, $\sigma_{act,fe}$, in each such fracture element which is larger than or equal to an ultimate tensile stress, $\sigma_{UTS,fe}$, of each individual fracture element, while, at the same time, the actual longitudinal element stress, $\sigma_{act,le}$, as developed in each one of these adjacent longitudinal elements 602 remains lower than their own respective yield stresses, $\sigma_{y,le}$, which can be stated in the equation:

$$\sigma_{act,le} \leq \sigma_{y,le} \text{ and } \sigma_{act,fe} \geq \sigma_{UTS,fe}.$$

Such break islands 604 have been described in detail and claimed in PCT application PCT/NL/2014/050837 of the present applicant, which is only published after the priority date of the present application. Its content is incorporated in the present application by reference in its entirety. PCT/NL/2014/050837 shows and explains break island 604 as shown in the present application in more detail. It is to be understood that the term "break island" is not meant to be limited to the embodiment shown in the present application but may be implemented in any suitable form, including any one of the examples shown in PCT/NL/2014/050837.

The cylindrical tube used to manufacture the intermediate cylindrical element 619 is cut such as to render finger-shaped elements 608 attached to rigid, ring-shaped element 610, as well as finger-shaped elements 611 of the longitudinal elements 602. Moreover, the cutting process is arranged such that, at the end of the cutting process, adjacent finger-shaped elements 608 and finger-shaped elements 611 have an interleaved position relative to one another.

The cutting process is also arranged such that it renders an open space 627 between each end face of finger-shaped element 611 and rigid, ring-shaped element 610, such that, in use of the steerable instrument, the finger-shaped elements 611 can freely move in a longitudinal direction between adjacent finger-shaped elements 608. However, when the cutting process is finished, preferably, each finger-shaped element 611 is still attached to an adjacent finger-shaped element 608 by one or more break islands 606. As explained above, such break islands 608 are designed such that, when in use of the steerable instrument finger-shaped elements 611 move in a longitudinal direction relative to adjacent finger-shaped elements 608, each break island 608 will break off from at least one of the adjacent finger-shaped elements 608, 611. This breaking apart will result in a situation where finger-shaped elements 608 can move freely relative to finger-shaped elements 611, and vice versa. Again, this breaking apart can be postponed until the steerable instrument is in its assembled state. This facilitates the manufacturing process seriously. These break islands 606 may have a circular shaped portion attached to adjacent finger-shaped elements 608, 611 by thin flexible bridges like the break islands 604. If desired, the break islands 606 may have any other suitable design including any one described in PCT/NL/2014/050837.

It is observed that, once break islands 606 are broken off, intermediate cylindrical element 619 falls apart into two independently moveable sections at either side of dotted line 613.

FIG. 8 shows how the set of cylindrical elements comprising cylindrical element 600 inserted in intermediate cylindrical element 619 is inserted in a cylindrical element 621. In the shown embodiment, cylindrical element 621 does not have longitudinal elements itself. Cylindrical element 621 is, preferably, made from a single cylindrical tube which may be made from the same material and may have the same thickness as inner protective cylindrical element 600 and intermediate cylindrical element 619.

The outer diameter of intermediate cylindrical element 619 and the inner diameter of intermediate cylindrical element 621 are chosen such that the clearance between the two is so small that they can easily move relative to one another in the longitudinal direction but that mutual radial play is kept at a minimum. The clearance may be in a range of 0.02 to 0.1 mm. Preferably, the intermediate cylindrical element 621 is made from a single cylindrical tube of any suitable material that may be the same material as the one from inner protective cylindrical element 600. The thickness of that tube depends on its application. For medical applications the thickness may be in a range of 0.1-2.0 mm, preferably 0.1-1.0 mm, more preferably 0.1-0.5 mm, and most preferably 0.2-0.4 mm. The diameter of the intermediate cylindrical element 621 depends on its application. For medical applications the diameter may be in a range of 0.5-20 mm, preferably 0.5-10 mm, more preferably 0.5-6 mm.

At the right-hand side of FIG. 8, i.e. the proximal side, intermediate cylindrical element 621 comprises a rigid, ring-shaped element 626 having an end 628. The rigid, ring-shaped element 626 is connected to a flexible portion 624 which extends along a predetermined distance of intermediate cylindrical element 621. Flexible portion 624 comprises one or more hinges such that flexible portion 624 can be deflected to a certain, predetermined angle relative to a central axis of the steerable instrument (i.e. the central axis of inner protective cylindrical element 600). Any suitable hinge known from the prior art can be used, e.g. the hinges shown in FIGS. 2c, 2d, 3a, 3b, and 3c of the present document. However, other hinges can be used including any suitable future one.

Towards the distal side of the intermediate cylindrical element 621, flexible portion 624 is connected to a rigid portion 622. The rigid portion 622 comprises rigid, cylindrical portions 612a, 612b which are attached to one another by means of longitudinally arranged connection elements 617. Preferably, these connection elements 617 have the form of straight strips with a constant width and thickness. Rigid, cylindrical portion 612b is connected to flexible portion 624.

As can better be seen in the enlarged view of FIG. 11, the rigid, cylindrical portions 612a, 612b and the connection elements 617 are arranged to define open spaces 631, one associated with one longitudinal element 602. Again, these open spaces 631 result from a cutting process, such as laser cutting. The cutting process is arranged such it also renders a sliding island 618 in each open space 631. When the cutting process is finished, preferably, each sliding island 618 is still attached to at least one of an adjacent connection element 617 and rigid, cylindrical portion 612a, 612b by means of one or more break islands 616, 620. Such break islands 616 have the same function as break islands 604 and 606 and may have the same form.

However, since break islands 616, 620 are connected to a connection element 617 and not to a longitudinal element, their definition is slightly different. I.e., here break islands 616, 620 are fracture elements which can be defined as follows. Each fracture element is configured and arranged to fracture when adjacent connection elements 617 to which each such fracture element is attached are moved in a longitudinal direction relative to one another such as to develop an actual fracture element stress, $\sigma_{act,fe}$, in each such fracture element which is larger than or equal to an ultimate tensile stress, $\sigma_{UTS,fe}$, of each individual fracture element, while, at the same time, the actual connection element stress, $\sigma_{act,ce}$, as developed in each one of these adjacent connection elements 617 remains lower than their own respective yield stresses, $\sigma_{y,ce}$, which can be stated in the equation:

$$\sigma_{act,ce} \leq \sigma_{y,ce} \text{ and } \sigma_{act,fe} \geq \sigma_{UTS,fe}.$$

For example, as shown in FIGS. 8 and 11, at the end of the cutting process sliding island 618 is attached to one of the adjacent connection elements 617 by means of a break island 616, 620 at either longitudinal end. The length of sliding island 618, as measured in the longitudinal direction, is shorter than the longitudinal length of open space 631 in which it is located. Thus, when in the assembled state of the steerable instrument break islands 616, 620 are broken off sliding island 618 can freely move in open space 631 along a predetermined distance. To provide the sliding islands 618 with a guiding function as will become apparent hereinafter, their width, as measured in a tangential direction, is, preferably at least along a predetermined portion of e.g. more than 50% of their total length, only slightly smaller than the width of open space 631, as measured in the tangential direction. In an embodiment, the difference between these two widths is less than 60 µm, preferably less than 40 µm.

During inserting intermediate cylindrical element 619 into intermediate cylindrical element 621, every sliding island 618 is aligned with one longitudinal element 602 now located at its inside. After the sliding islands 618 have been properly aligned with the longitudinal elements 602 each sliding island 618 is connected or attached to one longitudinal element 602. The connection/attachment may be to finger-shaped island 611 as is schematically indicated with dotted arrow 634 between FIGS. 8 and 7.

Such a connection/attachment can be made by welding, like laser welding. However, also a mechanical connection/attachment can be made, e.g., by means of a snap fit connection. Alternatively, glue can be used. The connection/attachment is preferably made when the longitudinal elements 602 are still attached to each other by means of break islands 604 at the distal end, the finger-shaped elements 611 are still attached to the finger-shaped elements 608 by means of the break islands 606 and the sliding islands 618 are still attached to at least one of the connection elements 617 and the rigid cylindrical portions 612a, 612b by means of break islands 616, 620. Moreover, the connection/attachment should be such that each sliding island 618 moves together with the longitudinal element 602 to which it is connected/attached with as little play as possible. This common movement of longitudinal elements 602 and respective sliding island 618 causes the break islands 616 and 620 to break off during the first time the longitudinal elements 602, after being connected/attached to the respective sliding islands 618, move relative to intermediate cylindrical element 621.

In order to provide stability to the steerable instrument, rigid ring-shaped element 610 of intermediate cylindrical element 619 is, preferably, connected/attached to rigid portion 612b of intermediate cylindrical element 621, as shown by dotted arrow 636 between FIGS. 8 and 7. This connection/attachment can be done by welding, like laser welding, or any suitable mechanical connection, like a snap fit connection. Alternatively, glue can be used. This connection/attachment is preferably such that rigid, ring-shaped element 610 and rigid portion 612b cannot move independently from each other.

Thus, when longitudinal elements 602 are connected/attached to sliding islands 618, they are guided in a longitudinal direction both by their finger-shaped elements 611 between finger-shaped elements 608 and by the sliding islands 618 in open spaces 631. Their possible tangential movement is limited by the width of the slits between their finger-shaped elements 611 and finger-shaped elements 608 and between the sliding islands 618 and adjacent connection elements 617.

As shown in FIG. 9, the set of cylindrical elements inserted into each other as shown in FIG. 8 and comprising inner cylindrical element 600, intermediate cylindrical element 619 and intermediate cylindrical element 621, is inserted in an intermediate cylindrical element 623.

The outer diameter of intermediate cylindrical element 621 and the inner diameter of intermediate cylindrical element 623 are chosen such that the clearance between the two is so small that they can easily move relative to one another in the longitudinal direction but that mutual radial play is kept at a minimum. The clearance may be in a range of 0.02 to 0.1 mm.

Preferably, the intermediate cylindrical element 623 is made from a single cylindrical tube of any suitable material that may be the same material as the one from inner protective cylindrical element 600. The thickness of that tube depends on its application. For medical applications the thickness may be in a range of 0.1-2.0 mm, preferably 0.1-1.0 mm, more preferably 0.1-0.5 mm, and most preferably 0.2-0.4 mm. The diameter of the intermediate cylindrical element 623 depends on its application. For medical applications the diameter may be in a range of 0.5-20 mm, preferably 0.5-10 mm, more preferably 0.5-6 mm.

At the left hand, distal, side, in the embodiment of FIG. 9, intermediate cylindrical element 623 comprises a rigid, ring-shaped element 642. The rigid, ring-shaped element 642 is provided with a set of finger-shaped elements 627.

At the right hand, proximal, side, in the embodiment of FIG. 9, intermediate cylindrical element 623 comprises a rigid, cylindrical portion 656. Towards the distal side, the rigid, cylindrical portion 656 is attached to one or more flexible longitudinal elements 633. In a portion of the intermediate cylindrical element 623 that should be aligned with flexible portion 624 of intermediate cylindrical element 621, the flexible longitudinal elements 633 should be flexible enough to allow deflection of the steerable instrument. To that end, in the embodiment as shown, the flexible longitudinal elements 633 have a relative small width measured in the tangential direction. Their width is, preferably, constant along their length. In order to ensure that the flexible longitudinal elements 633 are secured in the tangential direction in this flexible portion, flexible spacers 654 are provided between them. Any suitable design of spacers may be used, e.g. the ones described in not yet published application PCT/NL2015/050798 of the present applicant.

At the distal side of the flexible portion, each flexible longitudinal element 633 is attached to a longitudinal element 635 which may have a larger width to provide them with a certain desired strength. E.g., adjacent longitudinal elements 635 may substantially touch one another. Here, the term "substantially" indicates that adjacent longitudinal elements 635 can be as close as possible along at least part of their length, the mutual distance only being determined by the cutting process used to make slits 650 between them.

At their distal ends, the longitudinal elements 635 are provided with finger-shaped elements 646 that are each located between two adjacent finger-shaped elements 627.

Again, all the shown slits, open spaces and spacers are preferably made by cutting, like laser cutting, a cylindrical tube. At the end of the cutting process, the finger-shaped elements 646 are still attached to the finger-shaped elements 627 by means of break islands 644. Such break islands 644 have the same function as explained with reference to break islands 604, 606, 616, 620. Therefore, break islands 644 may have the same design as break islands 604, 606, 616, 620. Break islands 644, preferably, remain intact and attached to both finger-shaped elements 627 and 646 during the assembling process of the steerable instrument and will only be broken off by, e.g., a user after finishing the assembling process.

As indicated by a dotted arrow 638, each longitudinal element 635 is connected/attached to one sliding island 618, after proper tangential and longitudinal alignment of the intermediate cylindrical element 621 and intermediate cylindrical element 623 such that each longitudinal element 635 is aligned with one sliding island 618. Thus, in this embodiment, the number of longitudinal elements 635 equals the number of sliding islands 618, and equals the number of longitudinal elements 602 in intermediate cylindrical element 619. The connection/attachment can be made by welding, e.g. laser welding, or any suitable mechanical connection like a snap fit connection. Alternatively, glue can be used. Again any play in such a connection should be kept to a minimum.

As an alternative, one or more of the longitudinal elements 635 are provided with a flexible lip 648. Such a lip 648, can then, again after proper alignment, be connected/attached to one sliding island 618, e.g. by laser welding. The advantage of using such a lip 648 is that it is flexible in a radial direction and, thus, can cope with tolerances in internal/external diameters of the intermediate cylindrical elements 621, 623.

FIG. 9 shows that also intermediate cylindrical element 623 will be separated into two independently moveable sections, as indicated with dotted line 652, once the break islands 644 have been broken off. Then, the longitudinal elements 635 will be guided in their longitudinal direction both by their finger-shaped elements 646 each located between two adjacent finger-shaped elements 627 and by the respective sliding islands 618 to which they are connected/attached.

In order to provide enough stability to the steerable device and align all cylindrical elements properly to one another, preferably, proximal end 658 is connected/attached to proximal end 628 of intermediate cylindrical element 621, as indicated with dotted arrow 640 between FIGS. 9 and 8.

FIG. 10 shows how a last, outer protective cylindrical element 625 is shifted over the set of cylindrical elements shown in FIG. 9, including inner cylindrical element 600 and three intermediate cylindrical elements 619, 621 and 623. Of course, a plastic sleeve or the like may be shifted over at least one or more portions of the steerable instrument as is clear to persons skilled in the art.

Outer protective cylindrical element 625 has a flexible portion 666 that should be longitudinally aligned with flexible longitudinal elements 633 of intermediate cylindrical element 623 and with flexible portion 624 of intermediate cylindrical element 621. At opposite sides of the flexible portion 666, outer protective cylindrical element 625 is provided with bend-resistive portions 664 and 668. Preferably, all flexible portions of the steerable instrument are at least 5 times, but more preferably at least 10 times more flexible than the bend-resistive or rigid portions of the steerable instrument.

The outer diameter of intermediate cylindrical element 623 and the inner diameter of outer cylindrical element 625 are chosen such that the clearance between the two is so small that they can easily move relative to one another in the longitudinal direction but that mutual radial play is kept at a minimum. The clearance may be in a range of 0.02 to 0.1 mm. Preferably, the outer cylindrical element 625 is made from a single cylindrical tube of any suitable material that may be the same material as the one from inner protective cylindrical element 600. The thickness of that tube depends on its application. For medical applications the thickness may be in a range of 0.1-2.0 mm, preferably 0.1-1.0 mm, more preferably 0.1-0.5 mm, and most preferably 0.2-0.4 mm. The diameter of the outer cylindrical element 625 depends on its application. For medical applications the diameter may be in a range of 0.5-20 mm, preferably 0.5-10 mm, more preferably 0.5-6 mm.

In order to provide enough stability to the steerable device and align all cylindrical elements properly to one another, preferably, proximal end 670 is connected/attached to proximal end 658 of intermediate cylindrical element 623, as indicated with dotted arrow 662 between FIGS. 10 and 9. For the same reason, distal end 663 of outer cylindrical element 625 is connected/attached to intermediate cylindrical element 623, as indicated with dotted arrow 660 between FIGS. 10 and 9. Such connection/attachment may be made by (laser) welding or by mechanical means including a snap-fit connection. Alternatively, glue can be used.

FIG. 12 shows a cross section view of a steerable instrument in accordance with an embodiment of the invention in its assembled state, comprising a diameter adaptation section 164 as described with reference to FIGS. 6-11. The same reference numbers refer to the same elements/components as in earlier figures.

In the example of FIG. 12, inner cylindrical element 600, intermediate cylindrical elements 619, 621, 623 and outer cylindrical element 625 are all coaxially arranged about a common axis of symmetry 692. The diameter of inner cylindrical element 600 is smaller than the diameter of intermediate cylindrical element 619, which is smaller than the diameter of intermediate cylindrical element 621, which is smaller than the diameter of intermediate cylindrical element 623, which is smaller than the diameter of outer cylindrical element 625.

FIG. 12 shows how different sections of inner cylindrical element 600, intermediate cylindrical elements 619, 621, 623, and outer cylindrical element 625 are longitudinally aligned in order to form the cylindrical diameter adaptation section 164.

I.e. bend-resistive portion 668 of outer cylindrical element 625 is aligned with and connected/attached to rigid, cylindrical portion 656 of intermediate cylindrical element 623, whereas rigid, cylindrical portion 656 itself is aligned with and connected/attached to rigid, ring-shaped 626 of intermediate cylindrical element 621.

Similarly, flexible portion 666 of outer cylindrical element 625 is aligned with flexible longitudinal elements 633, as well as with flexible portion 624 of intermediate cylindrical element 621.

Longitudinal elements 635 of intermediate cylindrical element 623 are aligned with rigid, cylindrical portion 612b of intermediate cylindrical element 621, as well as with rigid, ring-shaped element 610 of intermediate cylindrical element 619.

Each longitudinal element 635 of intermediate cylindrical element 623 is, at its inside, connected/attached to the outside of one of the sliding islands 618 of intermediate cylindrical element 621. Moreover, each sliding island 618 is, at its inside, connected/attached to one of the longitudinal elements 602, possibly via finger-shaped element 611, of intermediate cylindrical element 619.

As best shown in FIG. 11, each sliding island 618 is located in an open space 631 allowing the sliding island 618 to be moved back and forth in the longitudinal direction in space 631 once break islands 616, 620 have been broken off from connection element 617. Such breaking off will happen once the sliding island 618 is connected/attached to longitudinal element 635 and to longitudinal element 602, and the distal end of the steerable instrument is deflected about the flexible part of the steerable instrument defined by flexible portion 666, flexible longitudinal elements 633 and flexible portion 624. I.e., such a deflection causes, for instance, the longitudinal element 635 at the upper side of FIG. 12 to be shifted to the right. Consequently, because this longitudinal element 635 is connected/attached to one sliding island 618 and to one longitudinal element 602, also that sliding island 618 and that longitudinal element 602 will shift to the right, effectively developing a force on the attachments of the break islands 616, 620 to the adjacent connection elements 617 and breaking them off from the connection elements 617. However, the longitudinal elements 635 remain connected/attached to a respective one of the longitudinal elements 602 via a respective sliding island 618.

Towards the distal side of the steerable instrument, the steerable instrument is, in an embodiment, similarly designed as the steerable instrument shown in FIG. 5b. Therefore, the same reference numbers in FIG. 12b refer to the same elements as in FIG. 5b. One difference between the embodiments of FIGS. 5b and 12 is that the device of FIG. 5b only shows 3 cylindrical elements inserted into one another, because the inner protective cylindrical element 600 and outer protective cylindrical element 625 are not shown.

In the arrangement of FIG. 12, inner protective cylindrical element 600 comprises a rigid portion as shown in FIG. 6 which is located at the proximal side of the steerable instrument. This rigid portion is, at its distal end, connected to a flexible portion 680 which may be made of one or more hinges like flexible portion 666. At its distal end, flexible portion 680 is connected to a rigid portion 681 which, at its distal end, is connected to a flexible portion 682. This flexible portion 682 is, at its distal end, connected to a rigid portion 683 which itself, at its distal end, connected to a flexible portion 684. Flexible portion 684 is, at its distal end, connected to a rigid portion 685 which may be a rigid ring. As will be evident to a person skilled in the art, inner protective cylindrical element 600 with all its rigid and flexible portions may be made from a single cylindrical tube, e.g. by laser cutting.

In the arrangement of FIG. 12, longitudinal elements 602 of intermediate cylindrical element 619 have a flexible portion 670 at the longitudinal location of flexible portion 680 of inner protective cylindrical element 600. At its distal end, each flexible portion 670 may be attached to a less flexible portion 671 which itself, at its distal end, may be connected to a flexible portion 672. Flexible portions 672 are located at the same longitudinal location as flexible portion 682 of inner protective cylindrical element 600. At its distal end, each flexible portion 672 may be attached to a less flexible portion 673 which itself, at its distal end, is attached to a flexible portion 674. Finally, all flexible portions 674, at their distal ends, are connected to a single rigid ring 675. Rigid ring 675 is attached to rigid portion 685 of inner protective cylindrical element 600, e.g. by laser welding or by any suitable mechanical connection including a snap-fit connection. Alternatively, glue can be used. As will be evident to a person skilled in the art, intermediate cylindrical element 619 with all its rigid portions, longitudinal elements, flexible portions, and less flexible portions may be made from a single cylindrical tube, e.g. by laser cutting.

In the arrangement of FIG. 12, rigid, cylindrical portion 612a of intermediate cylindrical element 621, at its distal end, is attached to a plurality of longitudinal elements. Each such longitudinal element is provided with a flexible portion 676 at the longitudinal location of flexible portion 680 of inner protective cylindrical element 600. At its distal end, each flexible portion 676 may be attached to a less flexible portion 677 of the longitudinal element which itself, at its distal end, may be connected to a flexible portion 678. Flexible portions 678 are located at the same longitudinal location as flexible portion 682 of inner protective cylindrical element 600. At its distal end, each flexible portion 678 is attached to a rigid portion 689 which has the form of a rigid ring. The rigid portion 689 is, at its distal end, attached to a flexible portion 690. The flexible portion 690 may be implemented by hinges like flexible portion 666. Finally, flexible portion 690, at its distal end, is connected to a single rigid ring 691. Rigid ring 691 may be attached to rigid ring 675 of inner intermediate cylindrical element 619, e.g. by laser welding or by any suitable mechanical connection including a snap-fit connection. Alternatively, glue can be used. As will be evident to a person skilled in the art, intermediate cylindrical element 621 with all its rigid portions, longitudinal elements, flexible portions, and less flexible portions may be made from a single cylindrical tube, e.g. by laser cutting.

In the arrangement of FIG. 12, intermediate cylindrical element 623 has different functions. As explained above, at its proximal side the intermediate cylindrical element 623 is provided with a plurality of longitudinal elements 635 which, at their distal ends, have finger-shaped elements 646. These finger-shaped elements 646 are interleaved with finger-shaped elements 627 (cf. FIG. 9). These finger-shaped elements 627 are, at their distal ends, attached to rigid, ring-shaped element 642. At its distal end, the rigid, ring-shaped element 642 is connected to a flexible portion 686 which is located at the same longitudinal location as flexible portion 680 of inner protective cylindrical element 600. Flexible portion 686 may be designed in the same way as flexible portion 666 of outer protective cylindrical element 625. At its distal end, flexible portion 686 is connected to a rigid, bend-resistive portion 687, preferably, designed such as to completely cover longitudinal elements 677 and, thus, protect them against dust, liquids, moisture, and other contaminations. At its distal end, the rigid, bend-resistive portion 687 is connected to a flexible portion 688 which may be designed in a similar way as flexible portion 666. Finally, at its distal end, flexible portion 688 is connected to a rigid, ring-shaped portion 691. Rigid, ring-shaped portion 691 is attached to rigid portion 689 of intermediate cylindrical element 621, e.g. by laser welding or by any suitable mechanical connection including a snap-fit connection. Alternatively, glue can be used. As will be evident to a person skilled in the art, intermediate cylindrical element 623 with all its rigid portions, longitudinal elements, flexible portions, and less flexible portions may be made from a single cylindrical tube, e.g. by laser cutting.

First actuation zone 15 at the proximal side of the steerable instrument is formed by flexible portion 666, flexible longitudinal elements 633, and flexible portion 624, respectively, which are connected/attached to rigid, ring-shaped elements 668, 656, and 626, respectively. By deflecting the first actuation zone 15 longitudinal elements 635 will move in a longitudinal direction of the steerable instrument.

As explained above, any longitudinal movement of one or more of the longitudinal elements 635 translates into a longitudinal movement of respective ones of the longitudinal elements 602 because each one of the longitudinal elements 635 is connected/attached to a respective one of the longitudinal elements 602 via a sliding island 618. Consequently bendable zone 152, which forms first deflectable zone 17, at the distal side will be deflected. Because longitudinal elements 635 are located at a greater distance from the axis of symmetry 692 of the steerable instrument than the longitudinal elements 602, a certain deflection angle of the first actuation zone 15 results in a larger deflection of deflectable zone 17 at the distal side. Thus, an amplification effect is obtained. Some of the amplification may be lost due to elasticity of the longitudinal elements 635, 602.

Similarly, flexible zone 156 forms second actuation zone 14 comprising flexible portion 686, flexible portions 676 of the longitudinal elements in the intermediate cylindrical element 623, flexible portions 670 of longitudinal elements 602, and flexible portion 680. By deflecting the steerable instrument about the second actuation zone 14 bendable zone 154, which forms deflectable zone 16, will be deflected too due to longitudinal movement of the longitudinal elements 678, 677, 676. Deflectable zone 16 comprises flexible portion 688, flexible portions 678 of the longitudinal elements in the intermediate cylindrical element 623, flexible portions 672 of longitudinal elements 602, and flexible portion 682.

As will be evident to persons skilled in the art, the longitudinal elements in the different cylindrical elements may be oriented in a spiral form such that a bending of the first and/or second actuation zone 14, 15 in a certain surface results in a deflection of the deflectable zones 16, 17 in a different surface with a different orientation. One preferred orientation change is in a range of 170–190°, more preferably in a range of 175–185°. Reference is made to FIG. 2h.

Diameter adaptation zone 164 is shown between actuation zones 14, 15. However, as shown in FIG. 5a, diameter adaptation zone 164 can, alternatively, equally well be located at the distal side of actuation zone 14.

Now, some alternative embodiments are briefly explained.

First of all, it is observed that in the above explanation of FIGS. 6-12 the increase of the distance to the axis of symmetry of longitudinal elements 602 to the longitudinal elements 635 equals the sum of the thickness of intermediate cylindrical element 619 and the thickness of intermediate cylindrical element 621. Alternatively, a longitudinal element in first cylindrical element can simply be attached, e.g. by laser welding or any desired mechanical connection, to a longitudinal element in a second cylindrical element that is adjacent to the first cylindrical element. As a further alternative, sliding island 618 may itself be attached to another sliding island in another cylindrical element adjacent to cylindrical element 621 in which sliding island 618 is located, such that there are two (or even more) sliding islands located between longitudinal elements 602 and 635. This would increase the amplification factor.

Sliding islands can be also used in an embodiment where they are attached to longitudinal elements arranged in a spiral form (cf. FIG. 2h). Such sliding islands can prevent out-of-plane reactions of the tip, support a linear load of flexible longitudinal elements and cause less fatigue.

As a further alternative, no sliding island 618 is used in space 631 but lip 648 of longitudinal element 635 is folded inwardly through space 631 such that it engages and is welded to longitudinal element 602.

A still further alternative embodiment of a cylindrical diameter adaptation section 164 is shown in FIGS. 13a and 13b. These figures show a mechanical connection between longitudinal element 635 and longitudinal element 602. Such a mechanical connection can be made by providing longitudinal element 635 with an inwardly (i.e. towards the axis of symmetry) extending lip 700. This lip 700 may result from a T-shaped longitudinal element 635 of which the upper two small branches are folded inwardly, as shown in FIG. 13a. Of course, if desired there may only be one such lip 700, or more than two such lips 700. Lip 700 is arranged such that, in the assembled state, the most extending portion of lip 700 is located in a hole 702 in longitudinal element 602. Preferably, that most extending portion of lip 700 has a tight fit into hole 702 such that play of lip 700 in hole 702 is kept to an absolute minimum.

FIG. 13b shows how such a lip extends through space 631 in cylindrical element 621. Thus, again longitudinal elements 635 are located at a distance from axis of symmetry 692 equal to the distance of longitudinal elements 602 from axis of symmetry 692 plus the thickness of cylindrical element 619 and of cylindrical element 621. Of course, such a lip 700 can be made smaller or larger. This lip 700 can be used to connect adjacent longitudinal elements in adjacent cylindrical elements or longitudinal elements divided by more than one cylindrical element.

Even though the present invention has been mainly explained with reference to the embodiment of FIGS. 6-12 in which the steerable instrument has two actuation zones at a proximal side of the instrument and two bendable zones at a distal side, each one being controlled by one actuation zone, it should be understood that the invention is not restricted to two such actuation zones and two such controlled bendable zones. It can be applied in an instrument having one or more actuation zones and one or more controlled bendable zones. Moreover, even though the embodiment of FIG. 5b has been used as a starting point for explaining the invention with reference to cylindrical diameter adaptation section 164 in FIGS. 6-12, the invention can also be applied in the embodiment of FIG. 5a with reference to cylindrical diameter adaptation section 162.

To summarize, in the above examples a steerable instrument has been described and explained with at least the following features.

The steerable instrument 10 is designed for endoscopic and/or invasive type of applications, such as in surgery, and comprises an elongated tubular body 18 having at least one actuation zone 14, 15 at a proximal side of the steerable instrument and at least one bendable zone 16, 17 at a distal side of the steerable instrument. The at least one actuation zone 14, 15 is arranged to control bending of the at least one flexible zone 16, 17 by means of a plurality of longitudinal elements. The steerable instrument has a cylindrical diameter adaptation section 164 comprising a first side and a second side. The longitudinal elements are located at a first distance from an axis of symmetry 692 of the steerable instrument at the first side and at a second distance from the axis of symmetry 692 at the second side, where the first distance is different from the second distance.

The longitudinal elements comprise at least a first set of one or more longitudinal elements 602 and a second set of one or more longitudinal elements 635.

The one or more longitudinal elements 602 of the first set of longitudinal elements are located at the first distance from the axis of symmetry 692 at the first side as well as within the cylindrical diameter adaptation section 164.

The one or more longitudinal elements 635 of the second set of longitudinal elements are located at the second distance from the axis of symmetry 692 at the second side as well as within the cylindrical diameter adaptation section 164.

Each one of the one or more longitudinal elements 602 of the first set of longitudinal elements overlaps with one of the one or more longitudinal elements 635 of the second set of longitudinal elements within the cylindrical diameter adaptation section 164 as seen in a radial direction from the axis of symmetry 692, and is at least one of connected and attached to the one of the one or more longitudinal elements 635 of the second set of longitudinal elements, such that a movement of the one of the one or more longitudinal elements 602 of the first set of longitudinal elements in a longitudinal direction of the steerable instrument results in a same movement of the one of the one or more longitudinal elements 635 of the second set of longitudinal elements in the longitudinal direction.

Advantages of the presented design may be as follows.

The proximal side of the steerable instrument can made from a rigid intact portion of a tube.

No longitudinal elements need to be guided to another diameter layer of the instrument during manufacturing, thus simplifying the manufacturing process.

The longitudinal elements undergo less stress and compression.

All flexible portions are cut in the same way resulting in less play between spacers and longitudinal elements.

A cylindrical element with sliding islands forms a mask during (laser) welding of the sliding islands to innerly located longitudinal elements. This prevents welding of adjacent longitudinal elements to one another or to other tube portions.

Sliding islands are guiding longitudinal elements when they move in a longitudinal direction and prevent tangential movement of them which also compensates torque.

The presented design can be used to implement more than one diameter adaptation section easily.

By using break islands, a tube can be separated into different independent sections (as indicated with dotted lines 613, 652) which can be used for different functions.

Spacers

A second aspect of the invention relates to using sliding islands as spacers and guiding elements between adjacent longitudinal elements in the same cylindrical element. This second aspect elaborates upon prior art disclosed in WO2009112060A of the present applicant. To illustrate this second aspect, first FIG. 8 and its related description from WO2009112060A will be repeated here. WO2009112060A FIG. 8 is copied here as FIG. 14a.

FIG. 14a shows an unrolled version of a part of an intermediate cylindrical element 810. The figure shows two end portions 831, 835 which are mutually connected by means of a plurality of longitudinal elements 800 of which two are shown. In this figure, the two adjacent longitudinal elements 802 are shown as having a first flexible portion 801 attached to end portion 831 and a second flexible portion 803 attached to end portion 835. The first flexible portion 801 is attached to the second flexible portion 803 by means of an intermediate portion 802 which may be more rigid than the first flexible portion 801 and the second flexible portion 802 e.g., at least twice as rigid. The end portions 831, 835 and the longitudinal elements 800 can be made by laser cutting from a single cylindrical tube.

The first flexible portions 801 and the second flexible portions 803, respectively, have a circumferential width such that there is a circumferential gap 804 and 805, respectively, between each pair of adjacent first flexible portions 801 and second flexible portions 803, respectively. The intermediate portions 802 have a circumferential width such that two adjacent intermediate portions 802 are substantially in contact with each other, meaning that they are only separated from one another by a slit remaining after laser cutting the single cylindrical tube to render the end portions X31, X35 and the longitudinal elements 800 connecting them.

In each gap 804 and 805, respectively, sliding islands 806 and 807, respectively, have been placed which sliding islands 806 and 807, respectively, have a circumferential width filling the width of the gap 804 and 805, respectively. Thus, sliding islands 806 and 807 provide guiding elements for the adjacent first flexible portions 801 and adjacent second flexible portions 803, respectively, such that they prevent substantial tangential movement of adjacent first flexible portions 801 relative to one another and of adjacent second flexible portions 803 relative to one another.

The sliding islands 806, 807 may be made by laser cutting them from the same single cylindrical tube from which the end portions 831, 835 and the longitudinal elements 800 have been made. Then, the sum of the separations at either sides between sliding island 806 and the first flexible portions 801 and between sliding island 807 and the second flexible portions 803 may be two times the width of a slit remaining after such laser cutting.

Free movement of the longitudinal elements 800 in the longitudinal direction is achieved in that in the longitudinal direction the sliding islands 806 and 807, respectively, do not completely fill up the entire space of the gaps 804 and 805, respectively, but leave a predetermined free space.

For the production of such a system as shown in FIG. 14a, as explained in WO2009112060A, it is possible to first make the intermediate cylindrical elements by means of, e.g., laser cutting from a single cylindrical tube, which results in an intermediate cylindrical element in which each sliding islands 806 and 807 are still connected either to an adjacent longitudinal element 800 or to end portions 831 or 835. In this form, the connection point between the sliding island element 806 and 807 and the remaining of the intermediate cylindrical element 810 remains intact when the intermediate cylindrical element 810 is shifted into another cylindrical element external to the intermediate cylindrical element 810, which is provided with holes coinciding with the connection points. Once the assembly is finished, the connection points can then be destroyed.

As also explained in WO2009112060A, the sliding islands 806 and 807 are not completely free from the remaining of the instrument, but each sliding island 806 and 807 is connected either to another cylindrical element either internal to or external to the intermediate cylindrical element 810. In the embodiment shown this has been achieved by welding at one point 808 and 809, respectively, the sliding islands 806 and 807 to an intermediate rigid portion of the other cylindrical element external or internal to the intermediate cylindrical element 810. In this way the longitudinal elements 800 are accurately guided by the sliding island 806 and 807 in the flexible portions of the instrument, but the sliding island element 806 and 807 themselves are not free to move whereby the control of movement has been improved.

FIG. 14b shows how sliding islands can be used as spacers between adjacent longitudinal elements which sliding islands are first connected to adjacent longitudinal elements by means of break islands which are later in the manufacturing process broken off such that the sliding islands can freely move in an open space between adjacent longitudinal elements. This breaking off process can be performed without needing any holes in other cylindrical elements to destroy connection points as disclosed in WO2009112060A.

FIG. 14b is based on FIG. 4 described above and the same reference numbers refer to the same components. So, second aspect of the invention is explained with reference to a steerable instrument with one actuation zone at a first, e.g. proximal, side and arranged to control deflection of a single bendable zone at a second other, e.g. distal, side of the instrument. The shown steerable instrument comprises a diameter adaptation zone at the first side. However, the steerable instrument according to the second aspect may have no or more than one diameter adaptation zone at any desired location. Moreover, the steerable instrument according to the second aspect may also have more than one actuation zone and more than one bendable zone, wherein a deflection of each one is controlled by one actuation zone by means of its own set of longitudinal elements and wherein the sets are arranged in one or more intermediate cylindrical elements.

During the manufacturing process, the following actions are performed.

Inner cylindrical element 2202 is provided with its flexible parts 2222 and 2224, and intermediate rigid part 2223. Inner cylindrical element 2202 is preferably produced from a single tube, e.g. by laser cutting. Its material and dimensions, respectively, are selected from the same materials and dimensions, respectively, as indicated above with reference to inner cylindrical element 600.

Intermediate cylindrical element 2203 is provided. It comprises rigid ring 2331 at the proximal side and rigid ring 2335 at its distal side. Rigid ring 2331 and rigid ring 2335 are attached to one another by means of a plurality of longitudinal elements 2338. Intermediate cylindrical element 2203 is preferably produced from a single tube, e.g. by laser cutting. Its material, diameter and thickness, respectively, are selected from the same materials, diameter and thickness, respectively, as indicated above with reference to intermediate cylindrical elements 619, 621, 623. Between adjacent longitudinal elements 2338, the intermediate cylindrical element 2203 comprises one or more sliding islands 618*a*, 618*b*, 618*c*. Each sliding island 618*a*, 618*b*, 618*c* is still attached to at least one adjacent longitudinal element 2338 by means of at least one break island 616*a*/620*a*, 616*b*/620*b*, 616*c*/620*c*. Each one of these break islands 616*a*/620*a*, 616*b*/620*b*, 616*c*/620*c* meet the requirements of the definition given above with reference to break islands 604, 606, 616, 620, 644.

At predetermined portions, sliding islands 618*a*, 618*b*, 618*c* are separated from adjacent longitudinal elements 2338 by means of a small slit which is not wider than as caused by the manufacturing process to cut into the cylindrical tube. Smallest widths of these slits may be between 5-50 μm, preferably between 15-30 μm, as resulting from e.g. laser cutting.

Inner cylindrical element 2202 is inserted into intermediate cylindrical element 2203 such that flexible parts 222 and 2224 are longitudinally aligned with flexible portions of longitudinal elements 2338.

In the shown example, after such alignment, sliding islands 618*a*, 618*b* and 618*c*, respectively, are longitudinally aligned with flexible part 2224, intermediate rigid part 2223, and flexible part 2222 of inner cylindrical element 2202, respectively. A portion of sliding island 618*a* is arranged such that it extends beyond flexible part 2224 as seen in the longitudinal direction. The other portion, which is longitudinally aligned with flexible part 2224 should be flexible in a longitudinal direction because, if not, the steerable instrument cannot be deflected about flexible part 2224. This can be done by making suitable transverse slits in that other portion of sliding island 618*a*, as persons skilled in the art will understand.

Similarly, a portion of sliding island 618*c* is arranged such that it extends beyond flexible part 2222 as seen in the longitudinal direction. The other portion, which is longitudinally aligned with flexible part 2222 should be flexible in a longitudinal direction because, if not, the steerable instrument cannot be deflected about flexible part 2222. This can be done by making suitable transverse slits in that other portion of sliding island 618*c*, as persons skilled in the art will understand.

Since sliding island 618*b* is entirely aligned with intermediate rigid part 2223 it need not be flexible in its longitudinal direction.

Now, sliding islands 618*a*, 618*b*, 618*c* can be attached to inner cylindrical element 2202. To that effect, each one of said sliding islands 618*a*, 618*b*, 618*c* is attached, preferably, to a location on a rigid part of inner cylindrical element 2202. The attachment is made on one or more locations on each sliding island 618*a*, 618*b*, 618*c*. Instead of these attachments, or in addition to them, the sliding islands 618*a*, 618*b*, 618*c* may be attached at one or more locations to outside cylindrical element 2204, as will be explained below.

The set of inner cylindrical element 2202 and intermediate cylindrical element 2203 is inserted into outer cylindrical element 2204. Flexible parts 2242 and 2244, respectively, are aligned with flexible parts 2222 and 2224, respectively.

Sliding island 618*b* is now aligned with intermediate rigid part 2243. Portions of sliding islands 618*a* and 618*c* are aligned with rigid parts of outer cylindrical element 2204 too.

As indicated with respective arrows 840, 841, 842, 843, 844, 845, 846, and 847 sliding islands 618*a*, 618*b*, 618*c* may be attached at one or more suitable locations to a rigid part of outer cylindrical element 2204.

It is observed that inner cylindrical element 2202 and outer cylindrical element 2204 need not be provided both. One of them is sufficient. Moreover, if they are both present, sliding islands 618*a*, 618*b*, 618*c* may be attached at one or more suitable locations to rigid parts of only one of inner cylindrical element 2202 and outer cylindrical element 2204.

After the inner cylindrical element 2202, intermediate cylindrical element 2203 and outer cylindrical element 2204 have been inserted into one another the flexible zone as defined by flexible parts 2222, 2242 and/or the flexible zone as defined by flexible parts 2224, 2244 is deflected. By doing so, a longitudinal force in longitudinal elements 2338 is applied resulting in a counter-force in respective break islands 616*a*, 620*a*, 616*b*, 620*b*, 616*c*, 620*c* such that they break off from the respective longitudinal elements 2338 to which they are attached. However, they remain attached to said inner and/or outer cylindrical element 2202, 2204 and will function as longitudinal guides between adjacent longitudinal elements 2338 which prevent tangential movement.

It is observed that exerting a longitudinal force in the longitudinal elements 2338 to let the break islands 616*a*, 620*a*, 616*b*, 620*b*, 616*c*, 620*c* break off may be generated in any desired way.

It will be clear to a person skilled in the art that the scope of the invention is not limited to the examples discussed in the foregoing, but that several amendments and modifications thereof are possible without deviating from the scope of the invention as defined in the attached claims. While the invention has been illustrated and described in detail in the figures and the description, such illustration and description are to be considered illustrative or exemplary only, and not restrictive. The present invention is not limited to the disclosed embodiments but comprises any combination of the disclosed embodiments that can come to an advantage.

Variations to the disclosed embodiments can be understood and effected by a person skilled in the art in practicing the claimed invention, from a study of the figures, the description and the attached claims. In the description and claims, the word "comprising" does not exclude other elements, and the indefinite article "a" or "an" does not exclude a plurality. In fact it is to be construed as meaning "at least one". The mere fact that certain features are recited in mutually different dependent claims does not indicate that a combination of these features cannot be used to advantage. Any reference signs in the claims should not be construed as limiting the scope of the invention. Features of the above described embodiments and aspects can be combined unless their combining results in evident technical conflicts.

The invention claimed is:

1. A steerable instrument for at least one of endoscopic and invasive type of applications, the instrument comprising
an elongated tubular body having at least a first actuation zone at a proximal side of the steerable instrument and at least a first bendable zone at a distal side of the steerable instrument, the first actuation zone configured to control bending of the first bendable zone by means of a plurality of longitudinal steering elements, the steerable instrument having a cylindrical diameter adaptation section located proximally from the first bendable zone and comprising a first side and a second side, wherein
the longitudinal steering elements comprise at least a first set of one or more longitudinal steering elements and a second set of one or more longitudinal steering elements,
said one or more longitudinal steering elements of the first set of longitudinal steering elements are defined by longitudinal slits provided in a wall of a first cylindrical element and are located at a first distance from an axis of symmetry at said first side as well as within said cylindrical diameter adaptation section, the first cylindrical element having a first radius equal to said first distance,
said one or more longitudinal steering elements of the second set of longitudinal steering elements are defined by longitudinal slits provided in a wall of a second cylindrical element and are located at a second distance from said axis of symmetry at said second side as well as within said cylindrical diameter adaptation section, said second distance being different from said first distance, the second cylindrical element having a second radius equal to said second distance,
each longitudinal steering element of the first set of one or more longitudinal steering elements is overlapping with one longitudinal steering element of the second set of one or more longitudinal steering elements within said cylindrical diameter adaptation section in an area of overlap as seen in a radial direction from said axis of symmetry, and each longitudinal steering element of the first set of one or more longitudinal elements is connected and/or attached to one longitudinal steering element of the second set of one or more longitudinal steering elements in the area of overlap, such that a movement of each longitudinal steering element of the first set of one or more longitudinal steering elements in a longitudinal direction of said steerable instrument results in a same movement of said one longitudinal steering element of the second set of one or more longitudinal steering elements to which it is connected and/or attached in said longitudinal direction.

2. The steerable instrument according to claim 1, wherein said first actuation zone is flexible and configured to control deflecting of said first bendable zone by deflecting said first actuation zone about a first angle relative to said axis of symmetry such that said first bendable zone is deflected about a second angle which is different from said first angle.

3. The steerable instrument according to claim 1, wherein said one of said one or more longitudinal steering elements of the second set of longitudinal steering elements is attached to a flexible longitudinal steering element which is also defined by longitudinal slits provided in the wall of said second cylindrical element and located outside said cylindrical diameter adaptation section and inside said first actuation zone.

4. The steerable instrument according to claim 1, wherein said steerable instrument comprises a third cylindrical element having a third radius between said first radius and second radius and being located between said first cylindrical element and said second cylindrical element, the third cylindrical element having one or more open spaces in said cylindrical diameter adaptation section, each open space being configured to allow said one of said one or more longitudinal steering elements of the first set of longitudinal steering elements to be connected or attached to, or both connected and attached to said one of said one or more longitudinal steering elements of the second set of longitudinal steering elements.

5. The steerable instrument according to claim 4, wherein said one of said one or more longitudinal steering elements of the second set of longitudinal steering elements is attached to a flexible longitudinal steering element which is also defined by longitudinal slits provided in the wall of said second cylindrical element and located outside said cylindrical diameter adaptation section and inside said first actuation zone, and said third cylindrical element is provided with a flexible portion inside said first actuation zone.

6. The steerable instrument according to claim 4, wherein a sliding island is provided in each said open space, each sliding island being at least one of connected to and attached to both said one of said one or more longitudinal steering elements of the first set of longitudinal steering elements and to said one of said one or more longitudinal steering elements of the second set of longitudinal steering elements, and each sliding island having a longitudinal size which is smaller than a longitudinal size of said open space.

7. The steerable instrument according to claim 4, wherein said one of said one or more longitudinal steering elements of the first set of longitudinal steering elements and said one of said one or more longitudinal steering elements of the second set of longitudinal steering elements are at least one of connected and attached to each other through said open space by means of a lip.

8. The steerable instrument according to claim 1, wherein said one of said one or more longitudinal steering elements of the first set of longitudinal steering elements and said one of said one or more longitudinal steering elements of the second set of longitudinal steering elements are attached to one another by means of at least one of a welding process and gluing.

9. The steerable instrument according to claim 1, wherein said one of said one or more longitudinal steering elements of the first set of longitudinal steering elements and said one of said one or more longitudinal steering elements of the second set of longitudinal steering elements are connected to one another by means of a mechanical connection.

10. The steerable instrument according to claim 1, wherein said elongated tubular body has a second actuation zone at said proximal side of the steerable instrument and a second bendable zone at said distal side of the steerable instrument, said second actuation zone being configured to control bending of said second bendable zone by means of an other plurality of longitudinal steering elements.

11. A method of producing the steerable instrument for endoscopic and/or invasive type of applications according to claim 6, the method comprising:
a. Providing said first cylindrical element,
b. Providing said third cylindrical element, said third cylindrical element comprising rigid, cylindrical portions attached to one another by connection elements, said cylindrical portions and connection elements defining an open space, said at least one sliding island being attached to at least one of said connection elements and said rigid, cylindrical portions by means of one or more break islands, c. Inserting said first cylindrical element into said third cylindrical element,
d. Aligning said at least one sliding island with said at least one of said one or more longitudinal elements of said first cylindrical element,
e. At least one of connecting and attaching said at least one sliding island to said at least one of said one or more longitudinal steering elements of said first cylindrical element,
f. Providing said second cylindrical element and inserting said first cylindrical element and said third cylindrical element into said second cylindrical element,
g. Aligning said at least one sliding island with said at least one of said one or more longitudinal steering elements of said second cylindrical element,
h. At least one of connecting and attaching said at least one sliding island to said at least one of said one or more longitudinal steering elements of said second cylindrical element,
i. Breaking off said one or more break islands by moving said at least one sliding island in said open space such that said at least one sliding island can freely move in said open space.

12. The method according to claim 11, wherein said action i is performed by moving said at least one of said one or more longitudinal steering elements of said first cylindrical element and said at least one of said one or more longitudinal steering elements of said second cylindrical element relative to said third cylindrical element.

* * * * *